United States Patent [19]

Hatke et al.

[11] Patent Number: 5,206,807
[45] Date of Patent: Apr. 27, 1993

[54] NEONATAL CARDIORESPIROGRAPH INCORPORATING MULTI-VARIABLE DISPLAY AND MEMORY

[75] Inventors: Fred L. Hatke, Skillman; Ronald S. Kolarovic, Palmyra, both of N.J.; Reagh A. Stubbs, Rogers, Ark.; James A. Wise, Holland, Pa.

[73] Assignee: Air-Shields, Inc., Hatboro, Pa.

[21] Appl. No.: 310,678

[22] Filed: Feb. 16, 1989

[51] Int. Cl.$^5$ ............................................. G06F 15/42
[52] U.S. Cl. ............................... 364/413.03; 128/710; 128/716
[58] Field of Search ....................... 364/413.03, 413.02, 364/413.05, 413.06; 128/700, 709, 710, 716; 371/29.1

[56] References Cited

U.S. PATENT DOCUMENTS

| | | | |
|---|---|---|---|
| 3,608,542 | 9/1971 | Pacela | 128/923 |
| 3,881,467 | 5/1975 | Stanly et al. | 128/702 |
| 4,216,462 | 8/1980 | McGrath et al. | 364/413.03 |
| 4,228,506 | 10/1980 | Ripley et al. | 364/413.03 |
| 4,325,385 | 4/1982 | Holte | 128/712 |
| 4,356,475 | 10/1982 | Neumann et al. | 364/413.02 |
| 4,365,636 | 12/1982 | Barker | 128/716 |
| 4,403,215 | 9/1983 | Hofmann et al. | 128/723 |
| 4,531,527 | 7/1985 | Reinhold, Jr. et al. | 128/696 |
| 4,580,575 | 4/1986 | Birnbaum et al. | 128/716 |
| 4,630,614 | 12/1986 | Atlas | 128/721 |
| 4,779,199 | 10/1988 | Yoneda et al. | 364/413.03 |
| 4,794,532 | 12/1988 | Leckband et al. | 364/413.06 |

FOREIGN PATENT DOCUMENTS

8102832 10/1981 World Int. Prop. O. ......... 128/710

OTHER PUBLICATIONS

IEEE Cat. No. 79CH1474-6, 1979, Kriewall et al. "Neonatal Intensive Care Unit", pp. 247-279 (abstract only).
IEEE Proceedings of the Tenth Annual Northeast Bioengineering Conference, 1982, Sahakian et al. "A multi--microcomputer-based neonatal apnea monitor", pp. 151-156 (abstract only).
Patient Data Management System: System Description, Hewlett Packard Manual Part No. 78707-91998-9, 1982, pp. 1-1 to 2-23.
IEEE Engineering in Medicine and Biology Magazine, Sep. 1984, Hochberg "An Integrated Bedside Fetal Monitor and Obstetrical Data System", pp. 22-24.
Comput. Biol. Med., vol. 17, No. 4, 1987 Liu et al., "Infant's apnea, bradycardia and tachycardia monitor based on the Z-80 Microprocessor", pp. 269-277 (abstract only).
Comput. Biol. Med., vol. 14, No. 2, 1984, Divon et al. "Comprehensive Fetal Monitoring by Microcomputer—A Clinical Approach", pp. 151-157.
CASS: Computer Aided Sleep System, Advertisement.
"Prolonged Apnea and Cardia Arrythmias in Infants Discharged from Neonatal Intensive Care Units: Failure to Predict and Increased Risk for Sudden Death Syndrome", D. P. Southall et al., *Pediatrics*, vol. 70, No. 6, Dec. 1982.
"Home Pneumograms in Normal Infants", C. E. Hunt, et al., *Journal of Pediatrics*, vol. 106, No. 4, Apr. 1985.
"Day-to-Day Pneumogram Variability", C. E. Hunt, et al., *Pediatric Research*, vol. 19, No. 2, 1985.
"Apnea and Periodic Breathing in Normal Full-Term Infants During the First Twelve Months," D. H. Kelly, et al., *Pediatric Pulmonology* vol. 1, No. 4, Jul.-Aug. 1985.

(List continued on next page.)

Primary Examiner—Roy N. Envall, Jr.
Assistant Examiner—David Huntley
Attorney, Agent, or Firm—Ratner & Prestia

[57] ABSTRACT

A system and method for transducing, recording, and displaying information relating to cardiac and respiratory functions of an infant. The system and method allows immediate detection of apnea events and of bradycardia associated therewith, as well as presentation of historical charts of such events.

9 Claims, 20 Drawing Sheets

Microfiche Appendix Included
(16 Microfiche, 970 Pages)

OTHER PUBLICATIONS

"Pneumograms in Infants who Subsequently Died of Sudden Infant Death Syndrome," D. H. Kelly, et al. *Journal of Pediatrics*, vol. 109, No. 2, Aug. 1986.

"Undetected Episodes of Prolonged Apnea and Severe Bradycardia in Preterm Infants," D. P. Southall et al. *Pediatrics*, vol. 72, No. 4, Oct. 1983.

"Microprocessor-Based Long Term Cardiorespirography I. Heart Rate Changes and Apneic Attacks," H. Hornchen et al., *J. Perinat. Med.*, Nov. 1983.

"Incidence and Mechanism of Bradycardia During Apnoea in Preterm Infants," D. J. Henderson-Smart, et al., *Archives of Disease in Childhood*, 1986, 61.

"Periodic Breathing in Infants with Near-Miss Sudden Infant Death Syndrome," D. H. Kelly et al., *Pediatrics*, vol. 63, No. 3, Mar. 1979.

"Simplified Pneumographic Monitoring of Infants at Risk from Sudden Infant Death Syndrome," P. M. Rahilly et al., *Archives of Disease in Childhood*, 1984, 59.

"Neonatal Critical Care Monitoring," P. Rolfe, *Journal of Medical Engineering & Technology*, vol. 10, No. 3, May/Jun. 1986.

"Oxygen Monitoring of Neonates", P. Heinz.

"Lets End the Transcutaneous Vs. Oximetry Monitoring Controversy," *AARC Times*, Feb. 1987.

"Apnea and Bradycardia During Feeding in Infants Weighing >2000 Gm.," C. Guilleminault, *Journal of Pediatrics*, Jun. 1984.

"Onset of Breathing and Control of Respiration" A. H. Jansen et al., *Seminars in Perinatology*, vol. 12, No. 2, Apr. 1988.

"When is an Apnea not an Apnea?", C. F. George et al. *Respiratory Diseases*, 1985.

"Apnea in Infancy: Pathophysiology, Diagnosis and Treatment," A. N. Krauss, *New York State Journal of Medicine*, Feb. 1986.

Nellcor Advertisement.

"The Dose Response of Theophylline in the Treatment of Apnea of Prematurity," S. C. Muttitt et al., *The Journal of Pediatrics*, vol. 112, No. 1, Jan. 1988.

Hewlett Packard Advertisement.

Corometrics Advertisement.

Spacelabs Advertisement.

"Encyclopedia of Medical Devices and Instrumentation", vol. 3 by John G. Webster, 1988, pp. 2016, 2017, 2020–2025, 2033, and 2034.

NEONATAL CARDIORESPIROGRAPH INCORPORATING MULTI-VARIABLE DISPLAY AND MEMORY

A Microfiche Appendix including 16 microfiche is included in this application and is incorporated by reference. Each microfiche numbered 1 to 15 contains 62 frames plus one test target frame, for a total of 63 frames per microfiche. The last microfiche, numbered 16, contains 24 frames plus one test target frame for a total of 25 frames.

A portion of the disclosure of this patent document contains material which is subject to copyright protection. The copyright owner has no objection to the facsimile reproduction by anyone of the patent documents or the patent disclosure, as it appears in the Patent and Trademark patent file or records, but otherwise reserves all rights whatsoever.

BACKGROUND OF THE INVENTION

It has been recognized for a number of years that interruptions in breathing activity of infants, and particularly of premature infants, are significant medical events. Such interruptions of breathing are known as apnea. In addition to interruptions of breathing effort, another type of apnea involves a physical blockage or obstruction of the infant airway. This form of apnea is known as obstructive apnea and is not associated with a reduction in respiratory effort of the infant.

Although apnea by itself is a significant medical event, it is also recognized that when apnea is coupled with bradycardia (a significant slowing in heart rate unique to newborns), far more serious medical consequences may result. Various medical studies have proposed historical reconstruction of correlations between apneic events and bradycardic events for the purpose of diagnosis. Such reconstructions are typically performed using chart recording instruments having a common time scale and allowing these instruments to record long durations of patient information. Typically, many yards of chart paper are collected over a twelve-hour or longer duration and are aligned for visual inspection by an attending physician or researcher.

The instruments used in these correlation studies have included impedance pneumographs and conventional heart rate monitors.

Impedance pneumography is based on the principle that volume changes within a conducted electrical field are accompanied by changes in electrical resistance. Typical impedance pneumographs impose a small current (less than 0.3 ma) at 40 to 100 kiloHertz through electrodes placed on the infant chest wall.

Instruments which combine respiratory and cardiac information and plot the derived data on paper, display it on screen, or record it to a magnetic tape have been available for some time. In addition, many of these instruments are equipped with alarm circuitry which provides a visual or audible indication to attending medical personnel. These alarms are typically adjustable over some defined range. For example, periods of decreased breathing activity exceeding 20 seconds are determined to be apneic events and an apnea alarm is sounded.

A non-invasive technique for measuring oxygen saturation in active hemoglobin may be provided by a pulse oximeter (Nonin Medical Model 13030) which uses both visual and infra-red wavelengths of light transmission through, for example, a fingertip (or in the case of an infant, the big toe). Percent oxygen saturation of oxyhemoglobin is important as an indicator of the physiological condition which results from episodes of apnea, or episodes of apnea coupled with bradycardia.

SUMMARY OF THE INVENTION

According to the present invention, a system and method for displaying current and historical information related to apnea events in a human infant involve producing (via appropriate sensor and transducer systems) signals indicative of cardiac activity, respiratory effort, and relative saturation of oxyhemoglobin; processing these signals in a computer and displaying, simultaneously, on a single display device, visual representations of the signals in a manner which allows the signals to be correlated to provide information that is useful in the care of a human infant.

According to a further aspect of the invention, the method includes the steps of transmitting these signals to a computer (such as by electrical conduction, or signal modulation of RF or IR signals, or the like): receiving these signals into the computer; and calculating, storing, and simultaneously displaying to a user on a single visual display: (1) an electrocardiogram waveform, (2) smoothed value of a predetermined number of samples of the instantaneous heart rate, (3) smoothed value of a predetermined number of samples of the instantaneous oxyhemoglobin saturation, (4) respiratory effort, (5) transthoracic impedance, (6) smoothed value of a predetermined number of samples of the instantaneous respiration rate, (7) a graph of smoothed value of a predetermined number of samples of the instantaneous heart rate over a predetermined duration, (8) a graph of smoothed instantaneous oxyhemoglobin saturation over a predetermined duration, and (9) a graph of respiratory effort over a predetermined duration.

BRIEF DESCRIPTION OF THE INVENTION

Figure 1:
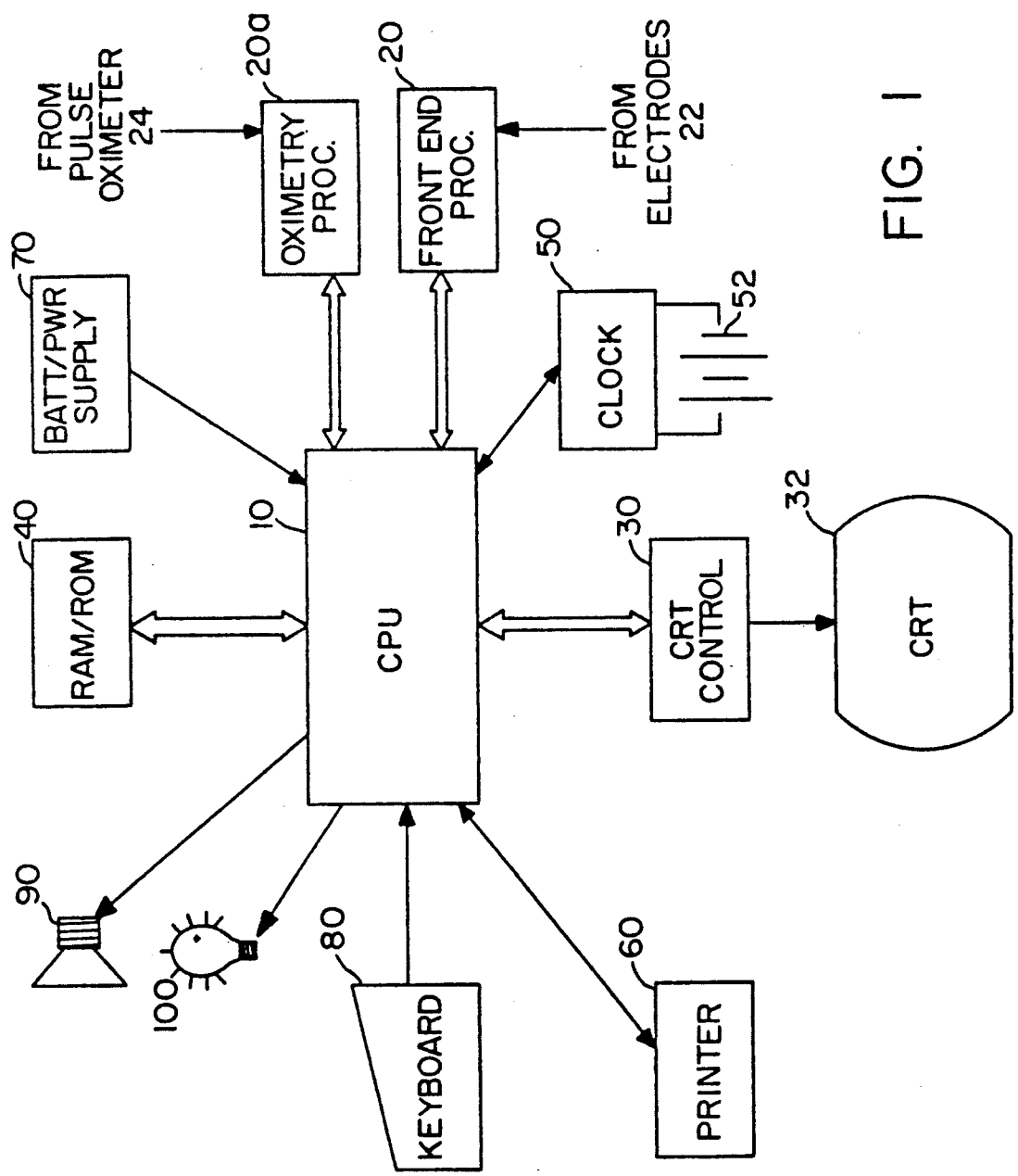
FIG. 1 is a block diagram of the monitoring system of the present invention.

The medical monitor of the present invention comprises a general purpose microprocessor-based computer which is programmed to process electrical signals emanating from patient transducers and to provide visual indications of processed patient information, audible indications of both patient and equipment alarm conditions, and self-diagnostic functions. The system takes its patient information inputs from a conventional pulse oximeter device and from electrodes attached to the patient chest wall and leg. Through these inputs, data relative to the infant's respiratory effort, and heart activity, are provided to a preprocessor module (front end board) which provides data input scaling, electrical isolation, and event interrupts to the main microcomputer system. Oxyhemoglobin saturation data from a separate transducer and micro-computer pre-processor is also provided to the main microcomputer system.

The microcomputer system is implemented as a multitasking architecture wherein discrete software processes share a single microprocessor according to a hierarchy of priorities. Real-time information is displayed to the user by various processes. In the main display mode of the system of the present invention, a real time electrocardiogram (ECG) is displayed. In addition, a common time axis which is adjustable to one minute, two minutes, or four minutes, displays smoothed (time integrated) real time heart rate, smoothed real time oxyhemoglobin saturation, and smoothed real time respiratory effort. This combined graph of real time heart rate and real time respiratory effort is termed a "cardiorespirogram" (CRG). In addition to displaying the various scales of these plots, individual instantaneous smoothed values for heart rate, oxyhemoglobin saturation, respiratory rate, indicator of perfusion, and transthoracic impedance are provided.

In response to key actuations by a user, additional information may be set and displayed including upper and lower alarm limits for heart rate, oxyhemoglobin saturation, and respiratory rate, as well as a duration alarm for apnea events.

In addition, a threshold limit for detection of bradycardia may be adjusted as well as the time scale on which the CRG is displayed.

The system of the present invention incorporates a digital memory sufficient to store 12 hours of patient events and data which are accumulated in five-minute intervals. The Pneumobar TM and Pneumoxybar TM trend displays, as well as their associated pointer detail modes, give an attending physician or nurse access to this historical data on screen or on an attached output printer, without the requirement that the information be continually printed or recorded to a storage device.

Correlations among apnea events of particular durations, bradycardia events coupled with apnea and levels of oxyhemoglobin saturation are graphically displayed in histogram form without requiring any chart or recorded data manipulation.

It is expected that the main display incorporating both ECG and CRG elements will be of central interest to primary caregivers (attending nurses), while the trend displays will be of primary interest to diagnosticians. For this reason, the system of the present invention defaults to its main display and automatically initiates that display whenever a preset alarm limit is crossed, or after a predetermined period in which there is no user interaction with the system.

DETAILED DESCRIPTION OF THE INVENTION

The monitor system and method of the present invention comprises an infant electrocardiograph and respirograph for use in neonatal intensive care units. The connection to the infant is by both standard electrodes for measuring transthoracic impedance and cardiac activity, and a standard neonatal pulse oximeter for measuring oxyhemoglobin saturation. The transduced signals are used within the monitor system to derive a smoothed heart rate, and a smoothed respiration rate which are provided with user definable high and low limits. The system also provides a user settable apnea delay alarm which is variable from 5 to 30 seconds in one second increments.

The cathode-ray tube display by which the monitor system of the present invention communicates with a user operates in eight distinct modes. These modes are termed start-up, main, trend one (or Pneumobar TM), trend two (or Pneumobar TM Pointer which is comprised of two sub-modes, each having a moveable pointer), trend three (Pneumoxybar TM), demo and service. Each screen mode is a separate function which is implemented by the system software contained within the monitor system. In each mode, the various displayed items and user inputs are individually defined.

Referring now to FIG. 1, there is shown a block diagram of the monitor system of the present invention. Central to the system is central processing unit (CPU) 10. In one embodiment of the present invention, CPU 10 is a Motorola 68000 microprocessor. As is conventional in the art, various support circuitry (not shown) is used to interface CPU 10 with other components of the system. Front end processor 20 is responsible for generating various data-derived interrupts and timing functions within the system. Front end processor 20 receives input by input line 22 from the patient electrodes. Pulse oximeter transducer signals are passed via line 24 to oximeter pre-processor 20a, and then to CPU 10. Based upon the occurrence of certain signal waveforms, front end processors 20 and 20a may interrupt CPU 10 in order to notify it that information is ready for further processing.

CPU 10 is also interfaced to CRT controller 30 (which in one implementation may be a 63484 device from, for instance, Hitachi). This controller allows the placement of discrete pixels at any location on the cathode-ray tube 32.

CPU 10 is interfaced through a standard address and data bus arrangement to memory 40 which may be a combination of read-only memory (ROM) and random access memory (RAM). In one implementation of the system of the present invention, the executing software program is stored in ROM and partially relocated to RAM for execution. In addition, data relative to system operation, time, and patient variable information is stored in memory 40 during system operation.

CPU 10 is further interfaced to battery backed-up clock 50 which comprises a real-time clock circuit coupled with a low-current drain random access memory. Battery 52 is used to independently power clock 50. During operation, clock 50 provides real-time information to CPU 10 and the random access memory portion of clock 50 is used to record operating parameter and time check data periodically during operaton. In the event of a power failure or other lapse, the stored information may be compared with available data in order to determine the duration of failure and to assess the validity of the current user variable settings.

CPU 10 is serially interfaced (with optical isolation) to printer 60 which may be a suitable all-points addressable output device. Because of maintenance constraints, it has been found that thermal printing devices which do not require disposables apart from paper are the most desirable type for use with the system of the present invention.

CPU 10 and all other peripheral devices are provided with power from power supply 70 which may optionally include a rechargeable battery. In addition to supplying power, power supply 70 also contains appropriate monitoring circuitry to allow CPU 10 to access the state of charge of the battery and also to allow proper execution of a start-up sequence when power is first applied to the system.

Data input from a user is accomplished through a set of key switches 80 which is interfaced to CPU 10. Depending upon the mode of operation, these key switches, used alone or in any one of several combinations, are individually decoded in software and their actions appropriately determined. According to the preferred embodiment of the present invention, there are seven key switches or buttons which are marked silent/reset, print, trend, pointer, set, up arrow, and down arrow.

In order to provide alarm indications and other feedback, CPU 10 is interfaced with audio circuitry (not shown) and a speaker 90. Various tones are generated to signal alarm and operating mode status and are transmitted to speaker 90 during operation. Similarly, alarm lights 100 are interfaced to CPU 10. In the preferred embodiment of the present invention, multiple alarm lights are located on the front and sides of the system case to provide a substantially full circle field of view. This is because, in typical operation, multiple units may be located in a small area, and a unit in alarm must be readily recognizable from any location in the room.

A complete discussion of the specific display features of the display modes of the present invention is contained in Microfiche Appendix I (comprising Air-Shields® System VI™ Infant Monitor with Pneumobar™ Displays and System VI-S™ Infant Monitor with Pneumobar™ and Pneumoxybar™ Displays Operators Manual, ©1989 Air-Shields Vickers)to this specification.

Figure 2:
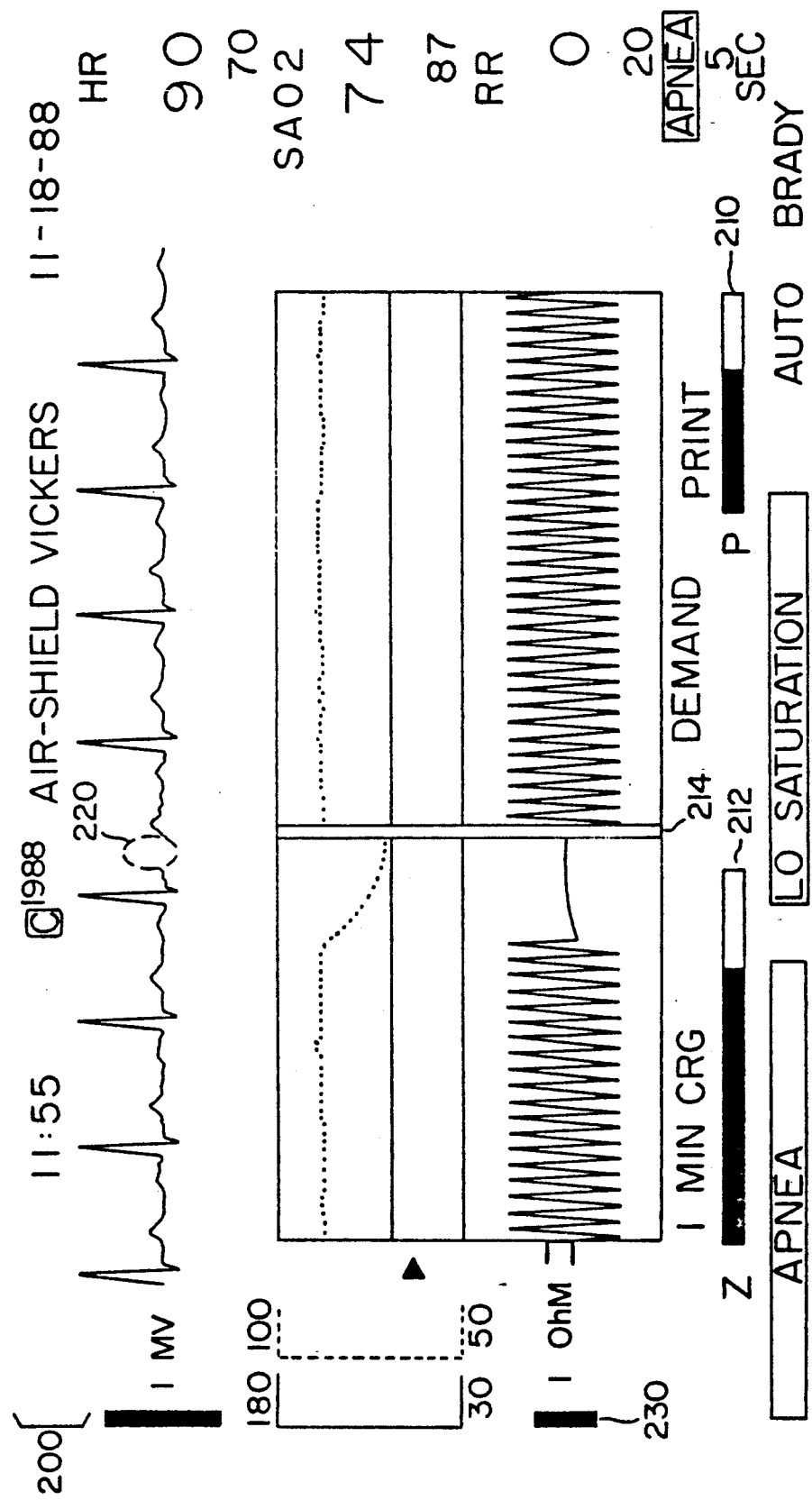
FIG. 2 is a representation of the main screen display of the monitoring system of the present invention.

Referring now to FIG. 2, there is shown a print out of the main mode screen of the system of the present invention. The description of that screen is given at sheets 2-9 through 2-18 of Appendix I as a description of the individual elements of the main display. In addition to the elements described therein, FIG. 2 includes a banner line 200 (displayed only on the printed rendition of the screen, and not on the video display itself) which includes the time and date at which the print out was made, a P bar 210 which is a graphical indication of changes in perfusion, and ECG break indicator 220 which is a graphical separation between newly plotted data (to the left of the blank area) and older data (to the right). The indicator 220 proceeds at a rate of 25 mm per second from left to right during operation. Respiration scale bar 230 indicates the impedance scale for the plot of respiratory effort.

It is the combination of displayed information on the main mode screen which makes it of primary usefulness to attending medical personnel (primarily nurses). Instantaneously available data reflecting the last one, two, or four minutes as well as an ongoing real time ECG, are invaluable in quickly evaluating an infant's condition. Furthermore, direct indications of perfusion and transthoracic impedance are important indicators of the condition of the sensor system. Still furthermore, because electrodes tend to deteriorate with time, the on-screen indication of transthoracic impedance 212 provides an indication of the quality of information being received by the monitor. As the electrodes age and the impedance increases, higher noise levels are experienced and less sensitivity is possible. Thus, the main mode display, in addition to providing significant instantaneous information about a patient, also provides an indication of when a renewal of the sensor electrodes is required Furthermore, the message center area of the main mode display provides direct indications of both patient and monitor system status.

Moving bar indicator 214 provides a graphical separation between newly plotted information (immediately to the left of the bar) and the oldest information (immediately to the right). Depending upon the time scale selected for display, bar 214 completes a left-to-right traversal of the plot area in one, two, or four minutes.

It should again be noted that the main screen of FIG. 2 is a "real time" display of patient information, while the other screens described below contain principally historical and statistical information. For this reason, detection of an alarm condition, or a lack of user interaction with the system causes a reversion to the main screen.

Figure 3:
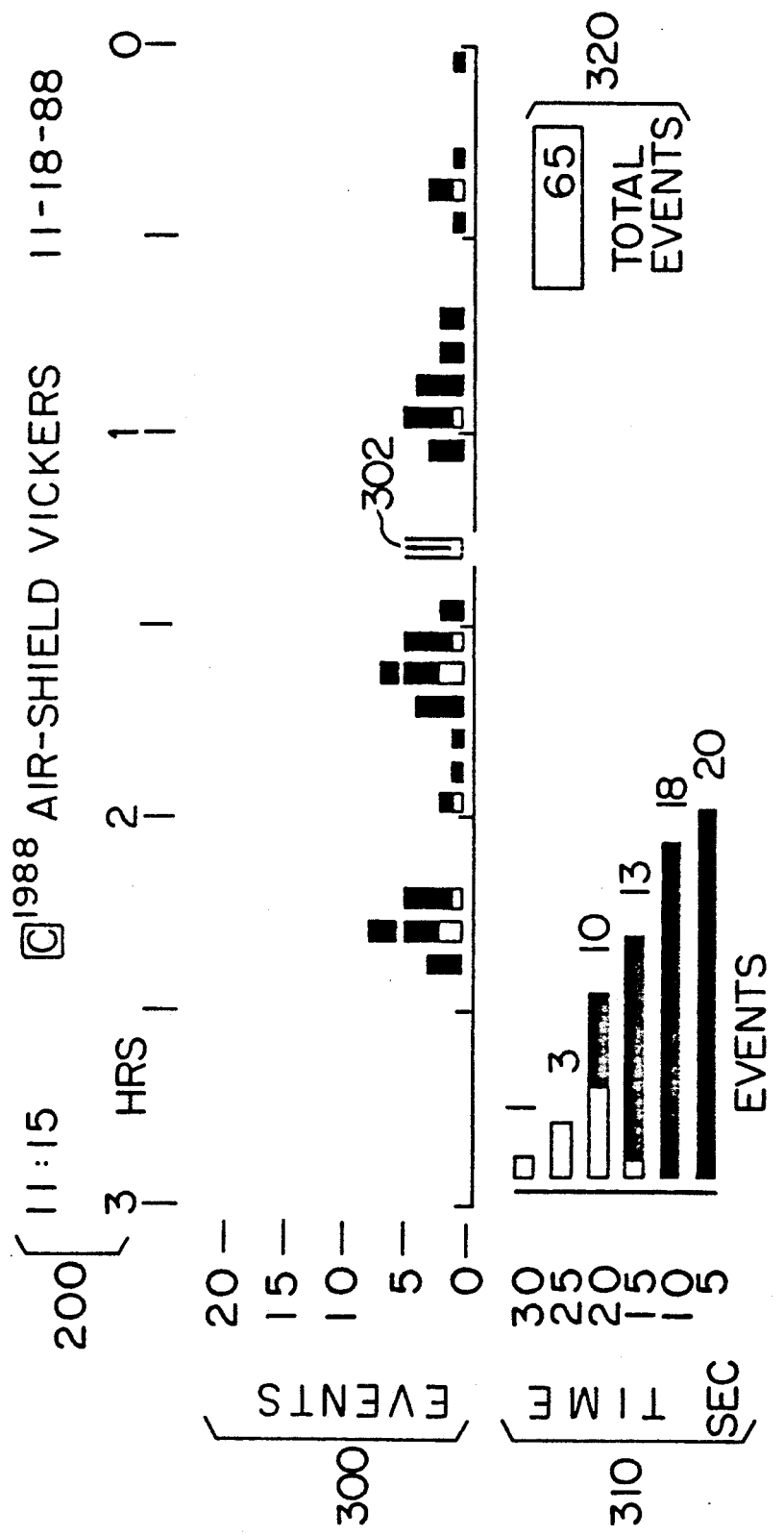
FIG. 3 is a representation of the first trend display screen or Pneumobar TM apnea histogram display.

Referring now to FIG. 3, there is shown a Trend One display or Pneumobar™ display generated according to the method of the present invention. A description of the Trend Displays is given at sheets 2-19 through 2-34 of Appendix I.

FIG. 3 depicts a histogram of three hours duration (read from right to left) which quantifies in five minute increments the incidence of reduced breathing effort or apnea. In this embodiment of the invention, the duration of an apneic event is determined as the amount of time between the end of one breath and the start of the second breath following the one breath. Additionally, a signal indicative of a respiratory effort is classified as a breath for the purpose of updating the calculation of the respiration rate if its amplitude is greater than or equal to twenty percent of a relative amplitude. This relative amplitude is a running average of the respiratory efforts of a predetermined number of preceding breaths. A print banner 200 (present only on the printout) indicates the time and date the print was produced. Histogram 300 plots time on the horizontal axis and numbers of apnea events (of five seconds duration or greater) on the vertical axis. Histogram 310 separately provides a sorted duration histogram for the various classes of events displayed during the three-hour period, and numeric display 320 indicates the total number of apneic events during the three-hour interval. Of special interest is histogram bar 302 which indicates the detection of an inoperable condition (power failure, electrode disconnect, or a similar event). Although the height of the hashed histogram bar represents the number of apneic events recorded during that particular interval, its hashed appearance signifies that the information recorded is somehow incomplete. Of additional interest are the individual bars within histogram 310. The 15, 20, 25, and 30 second bars are shown in outline or in partial outline indicating that a number of apneic events coincided with bradycardia. This is a significant clinical fact because adult patients normally experience acceleration of heart rate when breathing is reduced or obstructed. In infants, however, the opposite is often true. It will be noted that similar outlined sections appear in histogram 300 as well.

Figure 4:
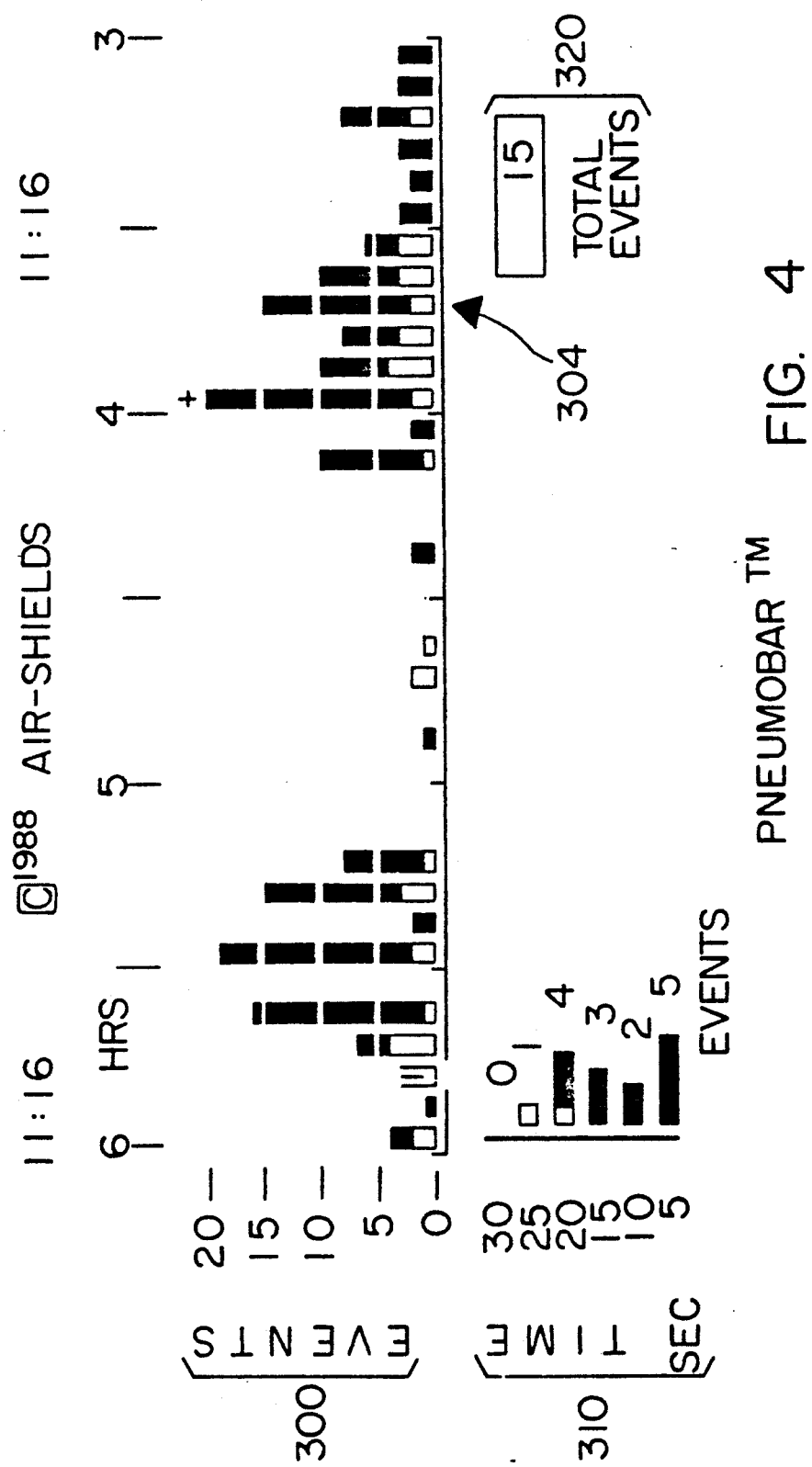
FIG. 4 is a representation of the second trend display screen or Pneumobar TM Pointer display.

Referring now to FIG. 4, there is shown a Trend Two (or Pneumobar™ Pointer) display. It will be noted that histogram 300 now displays a time interval from three to six hours in the past and that one of the histogram bars has exceeded its maximum recordation level of twenty events. In this instance, a small "+" symbol is displayed over the bar which has exceeded the display range in order to indicate this fact. A pointer 304 has been adjusted to indicate the particular histogram segment located at three hours forty-five minutes. The segment at three hours, fifty-five minutes is indicated to be out of range. In this mode, duration histogram 310 displays the duration only for the apnea events recorded between three hours and forty-five minutes and three hours fifty minutes as indicated by pointer 304, and indicator 320 displays the total number of events within that five minute interval. Such information is of relevance in determining the severity of apneic events. In particular, regardless of the alarm setting re-entered by the user, the system of the present invention continues to record all events of greater than five seconds' duration. It similarly records a bradycardia determination associated with apnea or with periodic breathing. In this way, a diagnostician may review particular epochs in the patient's recent history and determine, for instance, that an infant is experiencing periodic breathing or is experiencing, as shown in FIG. 4, a high incidence of apnea, the more lengthy events of which are coupled with reduced heart rate making them more threatening.

Figure 5:
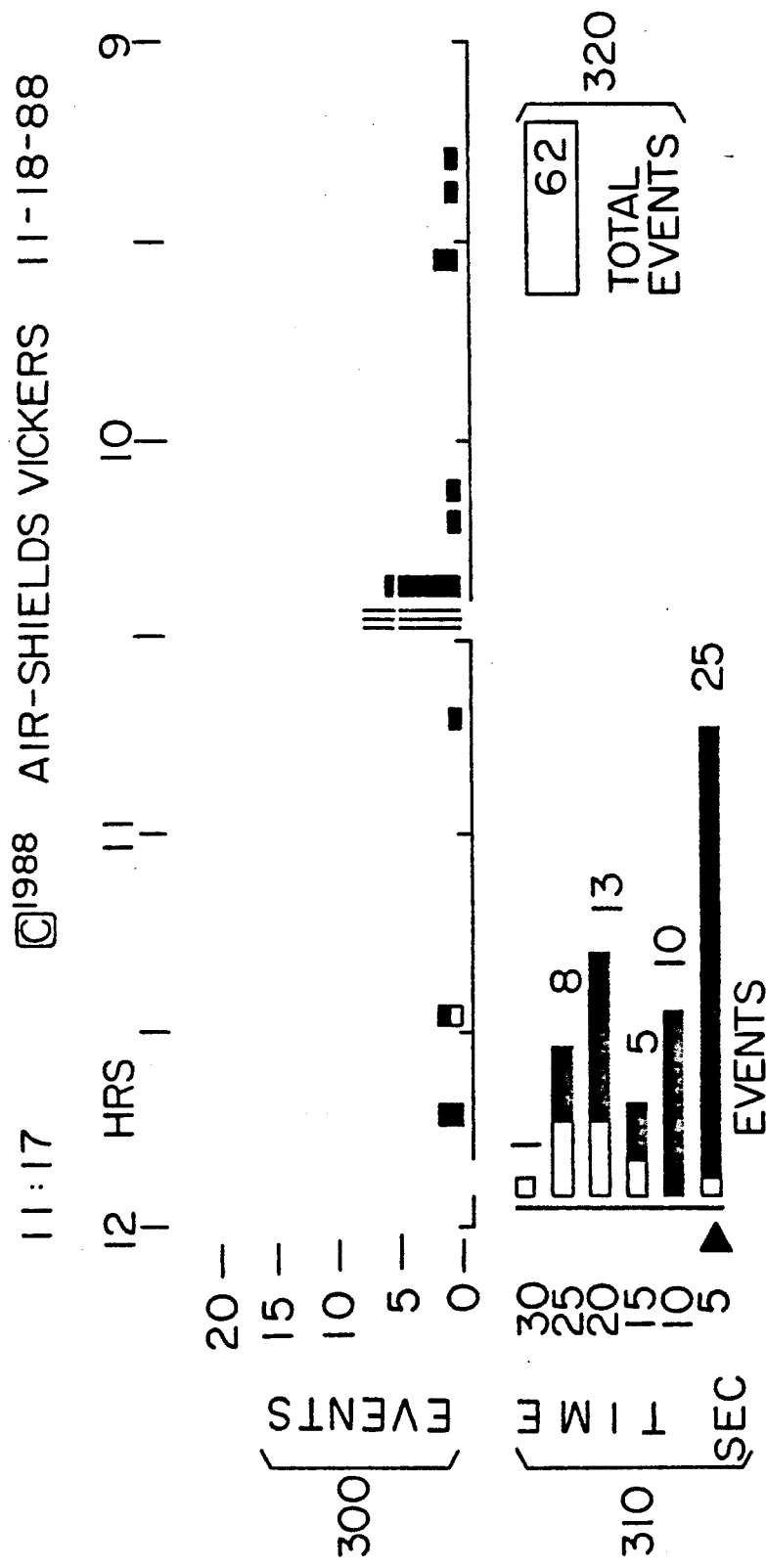
FIG. 5 is a representation of the second trend display screen in an alternate mode, or Pneumobar TM Pointer Mode Two display.

Referring now to FIG. 5, a second pointer mode illustrates the time-distribution of apnea events of a given duration. Examination of this information enables the clinician to make valuable clinical judgements including differentiation of "periodic breathing" from apneas, as well as correlation of external events, such as administration of medication or waking of the infant by the apnea alarm, with apnea events. This, too, assists a diagnositician in review of a patient's history.

Figure 6:
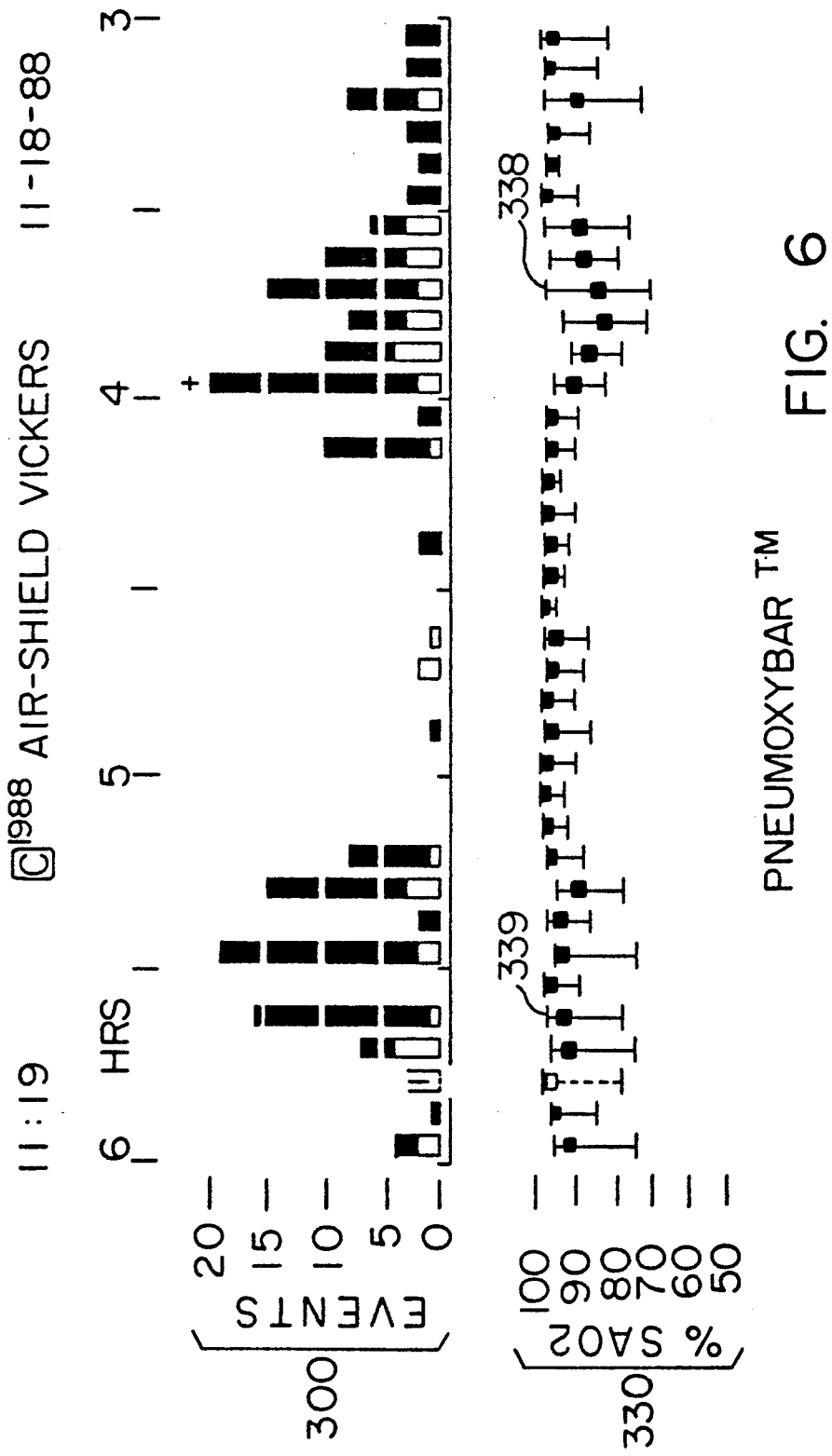
FIG. 6 is a representation of the third trend display of the present monitor or the Pneumoxybar TM apnea/oxyhemoglobin saturation time histogram.

Referring now to FIG. 6, there is shown a third type of trend display according to the method of the present invention. This display, termed a Pneumoxybar TM display, retains histogram 300 (and displays data identical to that of FIG. 4.) In addition, a display of oxyhemoglobin saturation is added in graph 330. For each five minute interval, the minimum value of oxyhemoglobin saturation in percent, the maximum value, and the average for that five minute interval are displayed as an "I" beam with a superimposed block market. By referring to the display 330, a diagnostician may determine the actual impact which apneas or apneas coupled with bradycardia had on the infant. By reference to plot element 338, it can be discerned that in the same period illustrated in FIG. 4 in which a total of thirty apnea events, two coupled with bradycardia, occurred, a range of oxyhemoglobin saturation from 50 to 99% was observed. However, the average saturation was 85%. Thus, it can be seen that the events of apnea during the particular time period had a far more severe effect than, for instance, the apneic episodes depicted at element 339 during which the range of saturations was more restricted, but the average saturation remained above 90%.

Figure 7:
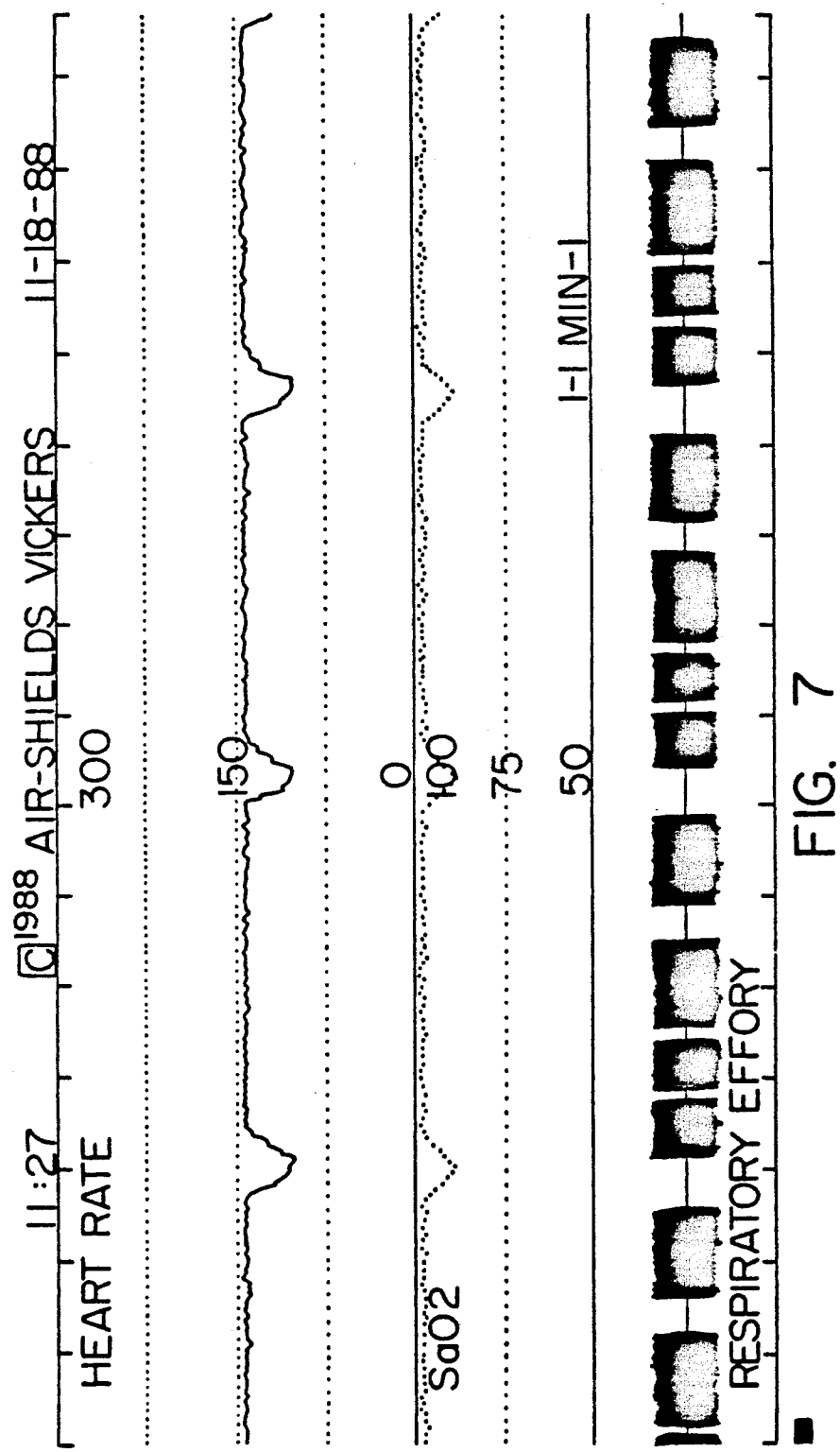
FIG. 7 is a printout produced by a continuous printout mode of the system of the present invention.

FIG. 7 is a portion of a continuous printout produced at real time by the system of the present invention. This printout depicts on a common user-selectable time scale, smoothed heart rate, oxyhemoglobin saturation, and respiratory effort. This printout corresponds closely to the multiple printouts which have heretofore been produced by separate instrumentation and manually aligned in order to search for correlations. During continuous print mode, screen prints of any display may be produced upon either alarm or demand. Such prints will be imbedded in the continuous print, which will queue data and will "catch up" at the conclusion of the screen print.

The system and method of the present invention is implemented as a multi-tasking computer system. Central to the function of that system is the software by which the various interactions with the user and display modes are generated. The multi-tasking aspect of the system is implemented in a system kernel which provides the basic structure for multi-tasking up to ten devices and twenty processes. Each device references a reserved area in memory which includes a status area and a ring buffer for storage of input and output data. Each process corresponds to a process block area reserved in memory which contains storage space for the CPU registers, flag storage, and a ring buffer for interprocess messages. Processes run as if each had a virtual microprocessor but can be suspended for indefinite periods of time. Consequently, each process also has its own stack storage area and both registers and stacks are stored or restored to and from this area during a context switch. Context switching is controlled by the kernel which determines when a process is ready to run and has sufficient priority to do so. In the preferred embodiment of the present invention, kernel commands are implemented as trap instructions. These include:

sleep
sleep_conditionally
time_read
interrupt_waiting
interrupt_send
interrupt_receive
message_send
message_waiting
message_receive
software_reset
system_reset
kernel_reinit In addition to trap instructions, the kernel module contains a number of subroutines accessed by outside programs such as interrupt service routines. These include:

put_interrupt
get_interrupt
test_interrupt which are used to manage interrupt data in ring buffers associated with device interrupts. Similarly, the subroutines:

put_message
get_message
test_message are used to manage interprocess messages in process ring buffers.

In addition to the kernel module, several other modules provide low-level support for the system of the present invention. These include a frame module which controls memory allocation for interrupt vectors, the stack, the serial transceiver circuitry, and the real time clock: the initialization module which defines global variables and data types for use by other modules: and the devices and arout modules which provide interrupt service routines for the peripheral devices.

In order of system priority, the following processes are implemented as independent modules in the multitasking environment controlled by the

POWER
ERROR

TIME
START-UP
SALES_DEMO
SERVICE
INTEGRITY
AUDIO
DISPLAY
PROCESS_DATA
TREND
ALARMS
SET
BUTTONS
SERIAL
PRINT
IDLE

The Microfiche Appendix contains the source code for these modules, in 68000 macroassembly language.

Figure 8:
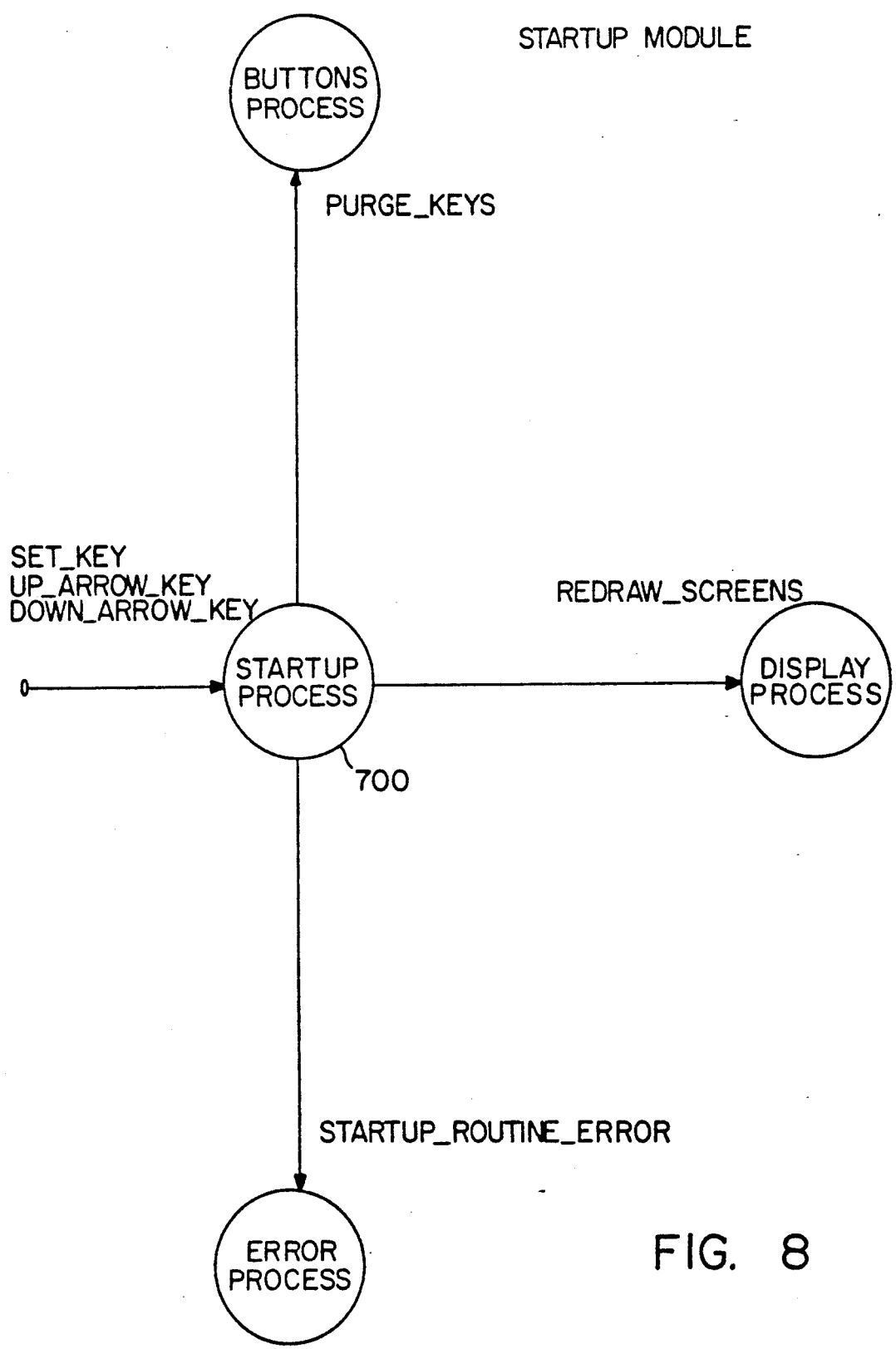
FIGS. 8–21 represent bubble diagrams of the software implemented processes comprising the monitoring system and method of the present invention.

Referring now to FIG. 8 there is shown a bubble diagram of the relations between the start-up process and other processes comprising the system of the present invention. The start-up process 700 is capable of receiving messages through a message receive trap instruction to the kernel. These messages may be SET_KEY, UP_ARROW, or DOWN_ARROW key. The start-up process may also send messages. These messages include PURGE_KEYS, REDRAW_SCREENS, and START-UP_ROUTINE_ERROR. Messages sent by this start-up process are received by other processes as depicted in FIG. 7. The start-up module is initiated after various system functions including the kernel have been initialized through a power-on reset sequence from the system hardware. The start-up module first displays a start-up message on the CRT for a predetermined period of time and then conducts an internal test of both random access memory and read only memory. Should either of these tests fail, a system failure message is displayed and the sleep trap instruction is issued. If both tests are passed, a short sleep trap is initiated to permit other processes to run briefly. On reactivation, if the start-up screen is still displayed, a PURGE_KEYS message is sent to the BUTTONS procedure, a REDRAW_SCREENS message is sent to the DISPLAY process, and the displayed screen is set to MAIN_DISPLAY. A message receive trap then allows for user entry of the set key, the up-arrow key or the down-arrow key. Actuation of any other key is ignored.

The setting routine allows the user to set the day, month, year, hour and minute by actuation of the up and down arrow keys to increment and decrement the value displayed, and by repeatedly actuating the set key to adjust the value which will be acted upon. If during the display of time and date information, no key is actuated for a period of greater than ten seconds, the start-up module is suspended with a message receive trap. It is, however, known that no other module within the system addresses messages to start-up and so the suspension is effectively permanent.

The MAIN/ERROR process includes software code for the error process, for the integrity process, and for the idle processes. The MAIN module also contains a table which defines process priority for the system as a whole.

Figure 9:
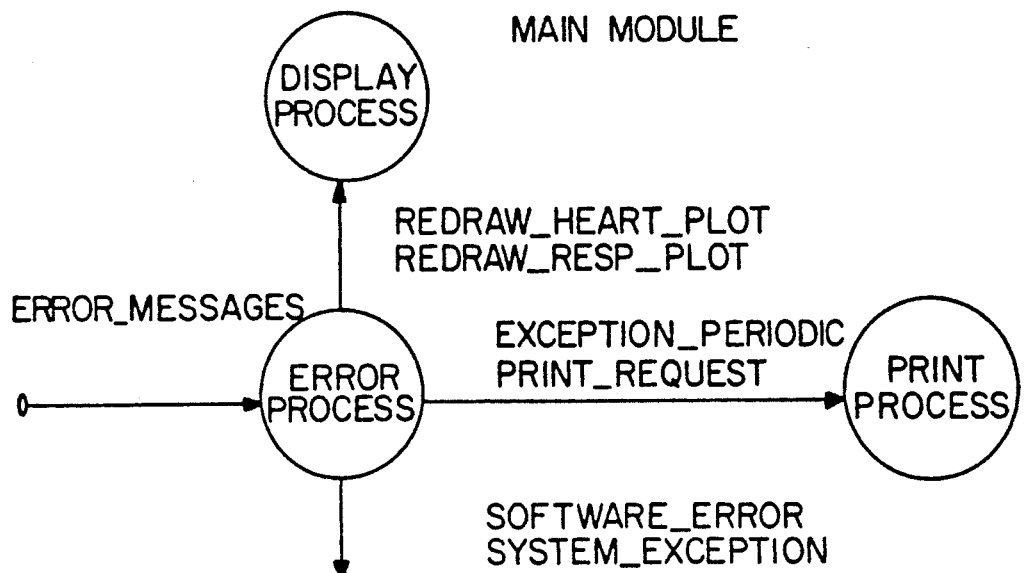

Referring now to FIG. 9, there is shown a bubble diagram for the MAIN process. As indicated in the figure, error messages are received by the ERROR process within the main module and are directed to the DISPLAY process and to the PRINT process, as appropriate. In addition, errors may trigger alarms which are instigated by messages sent to the ALARMS process. The INTEGRITY process and IDLE process are on-going within the main module, but neither send nor receive messages outside that module. The INTEGRITY process is also resets the "watch-dog timer" circuit which exists to prevent any process from executing for too long a period of time. If the watch-dog timer is not reset periodically, it can generate a system error exception which is handled by the ERROR process. The ERROR process maintains a total of the number of exceptions which it has received and when this total exceeds a predefined limit, a system failure mode is evoked which displays appropriate on-screen messages and effectively locks out the system. Software messages, such as invalid trap instructions, detected software errors, system restarts, and watch-dog timeouts cause the exception routine to reinitialize the system including reinitialization of the display, devices, data, and finally, reinitialization of the system kernel.

Figure 10:
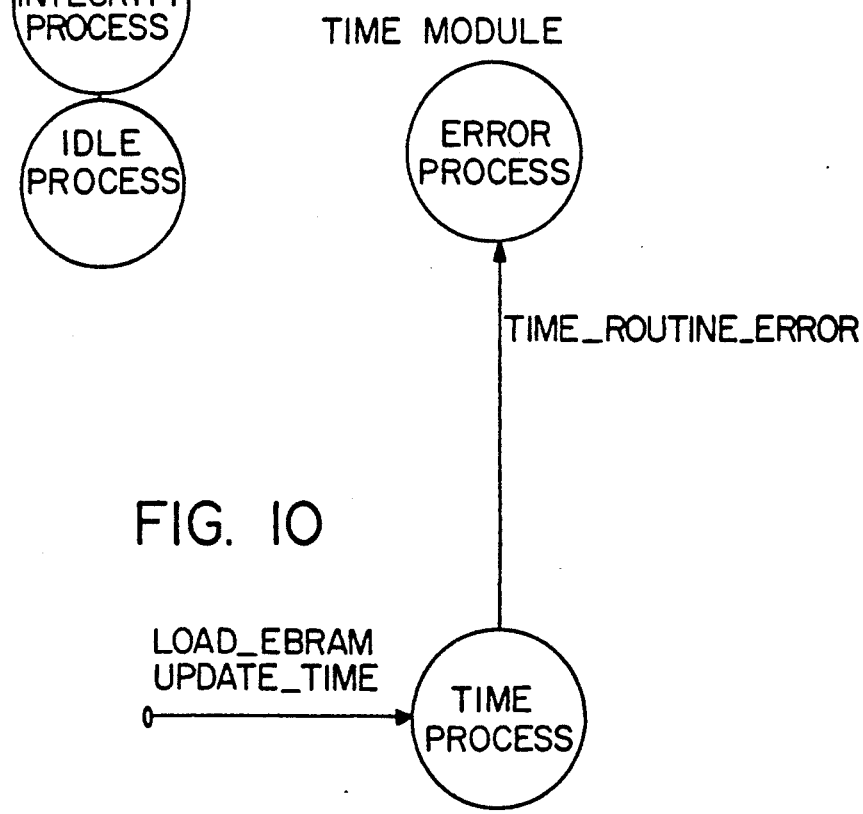

The TIME module depicted in FIG. 10 exists to up-date the random access memory on the real time clock chip. This random access memory, known as BBRAM (Battery Backed-up RAM) stores a time, alarm limits, and other user configurations, and a check-sum by which the information stored will be validated when retrieved. The time process can receive two messages: LOAD_BBRAM, and UP_DATE_TIME. The load instruction causes all system parameters which are global to the system to be stored in the real time clock chip random access memory, along with a computed check-sum of those values. The UP_DATE_TIME message causes the current time to be stored in a defined location in the Battery Backed-up RAM. This time is used by other processes to determine, for instance, the duration of a power failure.

Figure 11:
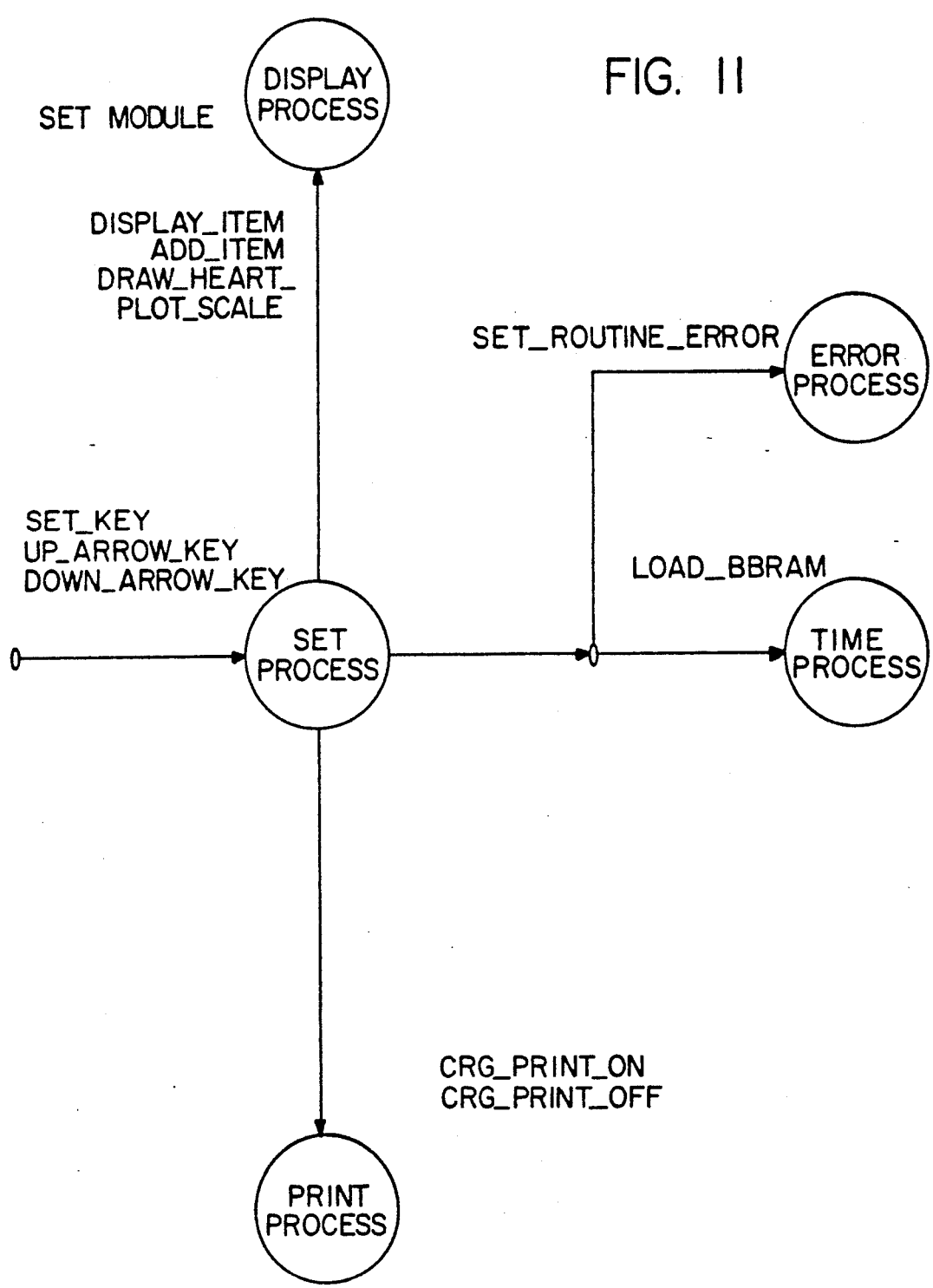

Referring now to FIG. 11, there is shown a bubble diagram of the message flow interrelationships concerning the SET process. The SET process receives messages from buttons indicating the actuation of the set key, the up-arrow key, and the down-arrow key. These three controls permit selection of each settable parameter of the monitor system of the present invention and incremental adjustment of each parameter's value. The SET process, in addition to permitting direct modification of these system parameters, communicates with the display process to control display modes such as time durations and inverse video indications, and communicates with the independent print process for initiating and terminating the real time print of cardiorespirogram information depicted in FIG. 7. In addition, the set process also communicates with the error process to indicate incorrect key actuations and the time process described above to up-date the Battery Backed-up Random Access Memory when a system parameter has been altered.

The set module is normally suspended in a message received trap instruction. When the buttons routine (described hereinafter) determines that a key actuation is intended for the set module, it passes a message to the set module which is then activated in its priority turn. The set module determines whether the SET_KEY has been depressed. If the SET_KEY is the one actuated, the currently displayed screen is determined and if it is the main or CRG display, the screen is placed in set mode which reveals the settable parameters (alarm limits, CRG time scale, apnea delay and other features as indicated in the user manual). Subsequent actuations of the SET_KEY cycle through each settable system parameter, one at a time, while actuations of the up-arrow and down-arrow keys increment or decrement the currently active parameter as appropriate. Continuous actuation of a key permits it to automatically repeat, thus allowing for rapid adjustment of a value. At the conclusion of set operations, or if no key strokes are received for a predetermined period of time (typically ten seconds), the display mode is returned to the main or CRG display and a message to up-date the Battery Backed-up Random Access Memory is forwarded to the time process.

Figure 12:
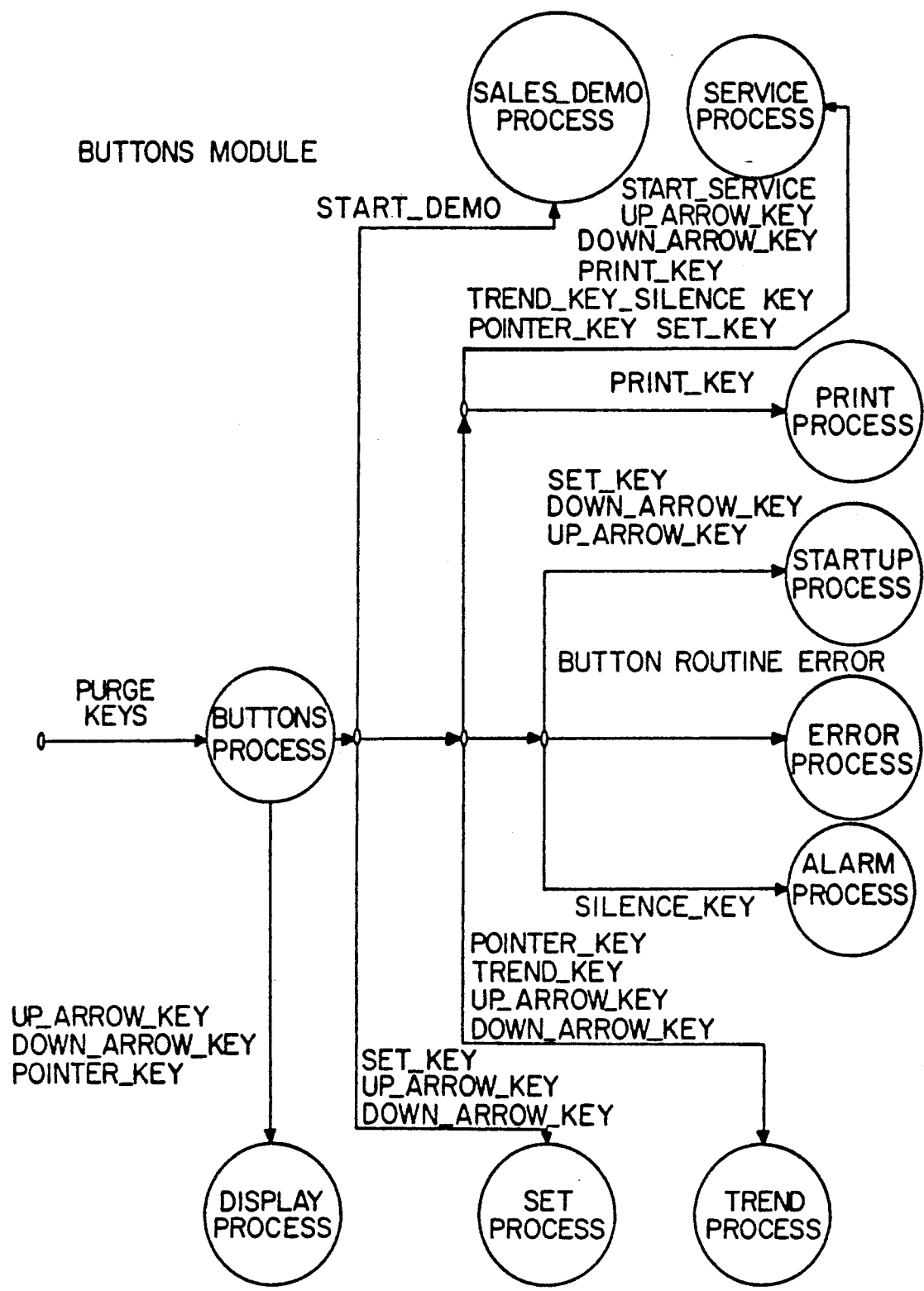

Referring now to FIG. 12, there is shown a bubble chart diagram of the message flow concerning the buttons process. This process is a relatively low-priority process but one which is central to the user control functions of the system of the present invention. The buttons process receives only one message, PURGE_KEYS, which flushes any pending key strokes from the ring buffer associated with the buttons process. The buttons process monitors the seven keys which may be user activated: silence, print, trend, pointer, set, up-arrow, and down-arrow. These keys may be actuated singly or in various combinations and are interpreted by buttons in accordance with predefined functions relative to each mode of the system of the present invention. The key definitions for each mode are summarized in Table I.

TABLE I

Key Functions, Startup

Silence—inactive
Print—inactive
Trend—inactive
Pointer—inactive
Set—inactive in base model, used to select element of time to set, if communication option is present
Up Arrow—inactive in base model, used to set time with communications option
Down Arrow—inactive in base model, used to set time with communication option
Silence-Set-Up Arrow—activate Sales Demo Silence-Set-Down Arrow and other keys—activate Service Mode Key Functions, CRG Display Silence—see Alarm Reporting
Print—will cause demand print of current display if printer present
Trend—Pneumobar TM Display 1 is entered
Pointer—inactive
Set—activates Set mode for CRG Display see Setting Parameters
Up Arrow—increments Time Scale in normal display mode and purges pending keystrokes, increments parameter in Set mode
Down Arrow—decrements Time Scale in normal display mode and purges pending keystrokes, decrements parameter in Set mode Key Functions, Pneumobar TM Display 1

Silence—inactive
Print—will cause demand print of current display if printer present
Trend—If no SATURATION option, CRG Display is entered. Else Pneumoxybar TM display entered
Pointer—Pneumobar Display 2 (or Pointer Mode 1) is entered
Set—inactive
Up Arrow—switches the time scale and display to the next 3 hours, with an upper limit of 9 to 12 hours, and purges pending keystrokes
Down Arrow—switches the time scale and display to the previous 3 hours, with low limit of 0 to 3 hours Key Functions, Pneumobar TM Display Pointer Mode 1

Silence—inactive
Print—will cause demand print of current display if printer present
Trend—CRG Display is entered, screen timeout is cleared or if saturation option present, Pneumoxybar TM screen is entered
Pointer—Pneumobar TM Display 3 (or Pointer Mode 2) is entered, screen timeout is initialized
Set—inactive
Up Arrow—moves cursor left one location, with wraparound, resets screen timeout
Down Arrow—moves cursor right one location, with wraparound, resets screen timeout Key Functions, Pneumobar TM Display Pointer Mode 2

Silence—inactive
Print—will cause demand print of current display if printer present
Trend—CRG Display is entered, screen timeout is cleared or if saturation option present, Pneumoxybar TM screen is entered
Pointer—Pneumobar TM Display Mode 1 is entered, screen timeout is initialized
Set—inactive
Up Arrow—moves cursor up one location, with wraparound, resets screen timeout
Down Arrow—moves cursor down one location, with wraparound, resets screen timeout Key Functions, Pneumoxybar TM Display Silence—inactive
Print—will cause demand print of current display if printer present
Trend—CRG display entered
Pointer—inactive
Set—inactive
Up Arrow—switches the time scale and display to the next 3 hours, with an upper limit of 9 to 12 hours, and purges pending keystrokes
Down Arrow—switches the time scale and display to the previous 3 hours, with low limit of 0 to 3 hours, and purges pending keystrokes Key Functions, Service Mode Silence—Active during key test only
Print—Active during key test only
Trend—Active during key test only
Pointer—Active during key test only
Set—Active during key test only
Up Arrow—Active during key test only
Down Arrow—Active during key test only

- Key Functions, Demo Mode

All keys function as if in other screen modes, Demo Mode message displayed

The buttons process normally remains in a sleep-conditionally trap instruction and periodically activates to check for interrupts. When an interrupt is received, the buttons process is activated to receive a button actuation. After receiving the identity of the button or buttons actuated, but before interpreting the action to be taken, buttons executes a message waiting trap instruction and if a message is waiting, executes a message received instruction to receive the PURGE_KEYS message. The PURGE_KEYS message causes the buttons process to purge the ring buffer associate with the process.

Interpretation of key actuations is performed by determining the current displayed screen and mode of the system of the present invention and issuing messages, as appropriate to those modes and screens to other processes which are suspended in a message received trap instruction. It will be appreciated that multiple keys may be actuated simultaneously and that such multiple key actuations constitute additional modalities of control (such as entry to the service and demo modes) available to the buttons process.

Figure 13:
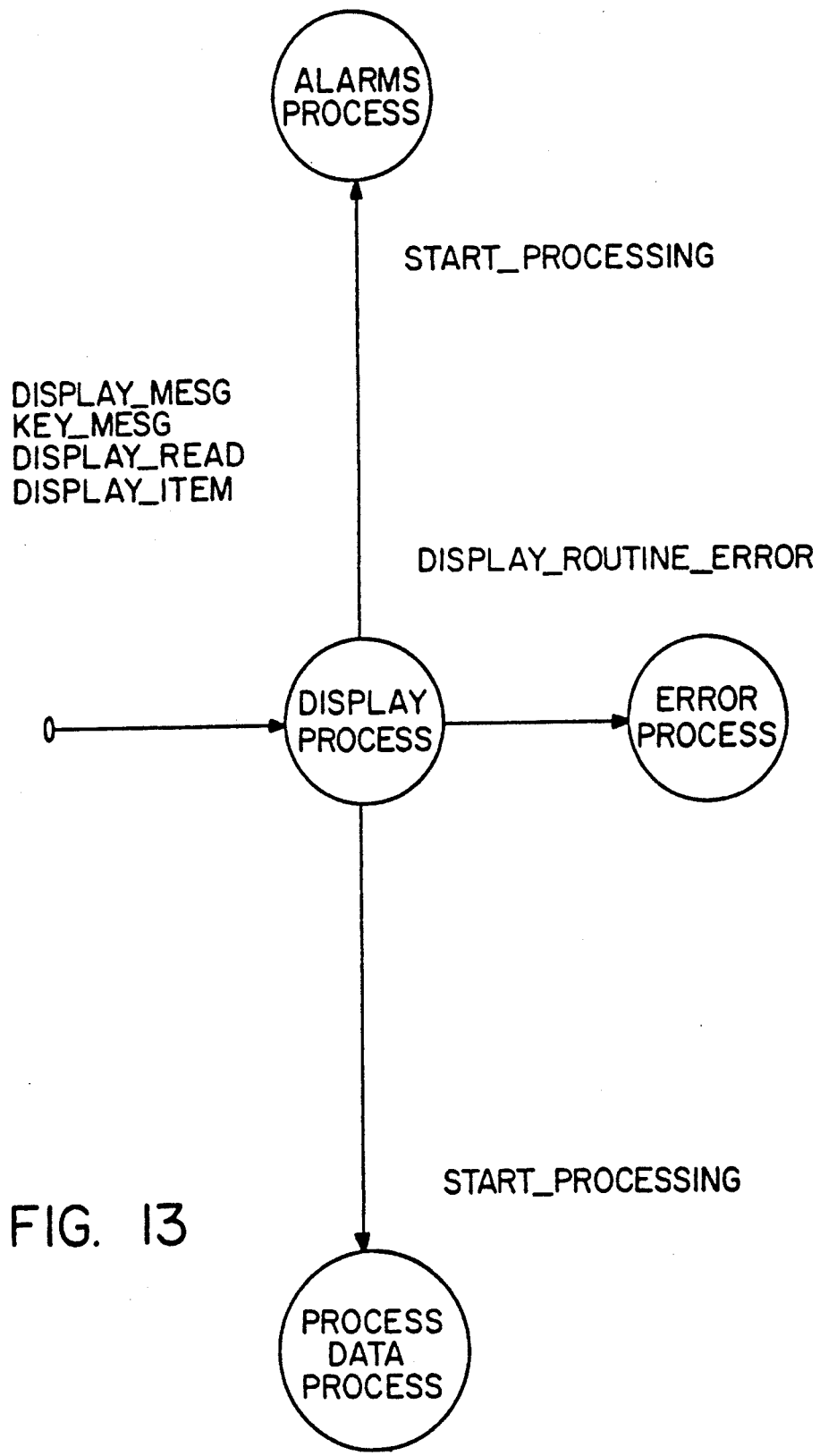

Referring now to FIG. 13, there is shown a bubble chart diagram of the message interrelationships for the display process module. The display process is responsible for managing the visual display screen and plotting all information except the real time ECG plot on the display screen. The message format received by the display process includes bits which are indicative of items to be displayed. These items include:
heart rate high limit
heart rate low limit
bradycardia threshold
saturation rate high limit
saturation rate low limit
respiration rate high limit
respiration rate low limit
apnea
CRG mode
print alarm mode
left message center
center message center
right message center
heart rate value
respiration rate value
saturation value
extra message center
bradycardia pointer
apnea alarm memory Because the display process controls the CRT controller hardware, it is also used during formatting of printouts in order to buffer partial screens and rotate them so that the aspect ratio of the screen may be accurately reproduced on the printer device.

The display process is subdivided into four principal modules. The display process relies upon a main display module for displaying and updating the main or CRG display of the system and a trend display module which manages display of all three trend displays (Pneumobar TM, Pnemobar TM Pointer, and Pneumoxybar TM). These modules, in turn, rely upon several lower level modules including PLOTS, GRAPHICS and FONT.

Figure 14:
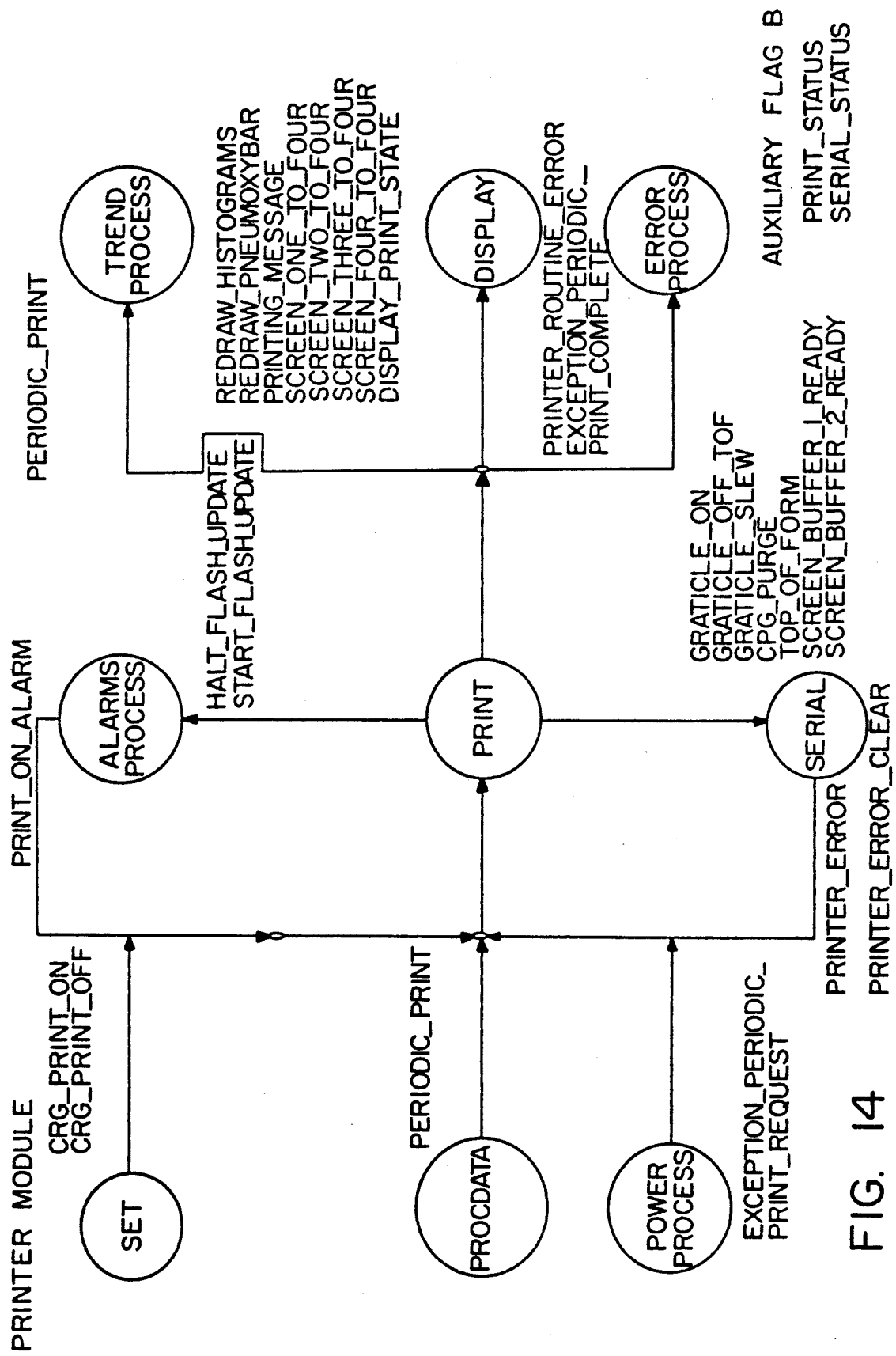

Referring now to FIG. 14, there is shown a bubble diagram of the print process of the present invention. Similar to the display process, print is highly interconnected by message flow with many other processes of the system. Print receives messages regarding the real time CRG print mode from the set process, regarding the periodic printing of information in normal operation from the process data process, emergency print requests from the power process (in order to preserve information before all power is lost). Print sends status messages to the alarms process which also may request that a printout be generated when an alarm is recognized. Print functions by requesting that the display, error and trend processes update appropriate screens in buffers controlled by the CRT controller hardware and then transfer those screens by way of the serial process to an external printer.

The print process receives all requests for printing regardless of their origin and notifies the display process to copy a particular screen into a reserved undisplayed screen buffer. The print process then enables the serial process which retrieves lines from that buffer, formats them appropriately and sends them serially to the external printer The print process also monitors the current status of the printer and generates exceptions which are handled by the error process. Printer status is also transmitted to the user by the sending of messages to the display process for placement on the active screen.

Figure 15:
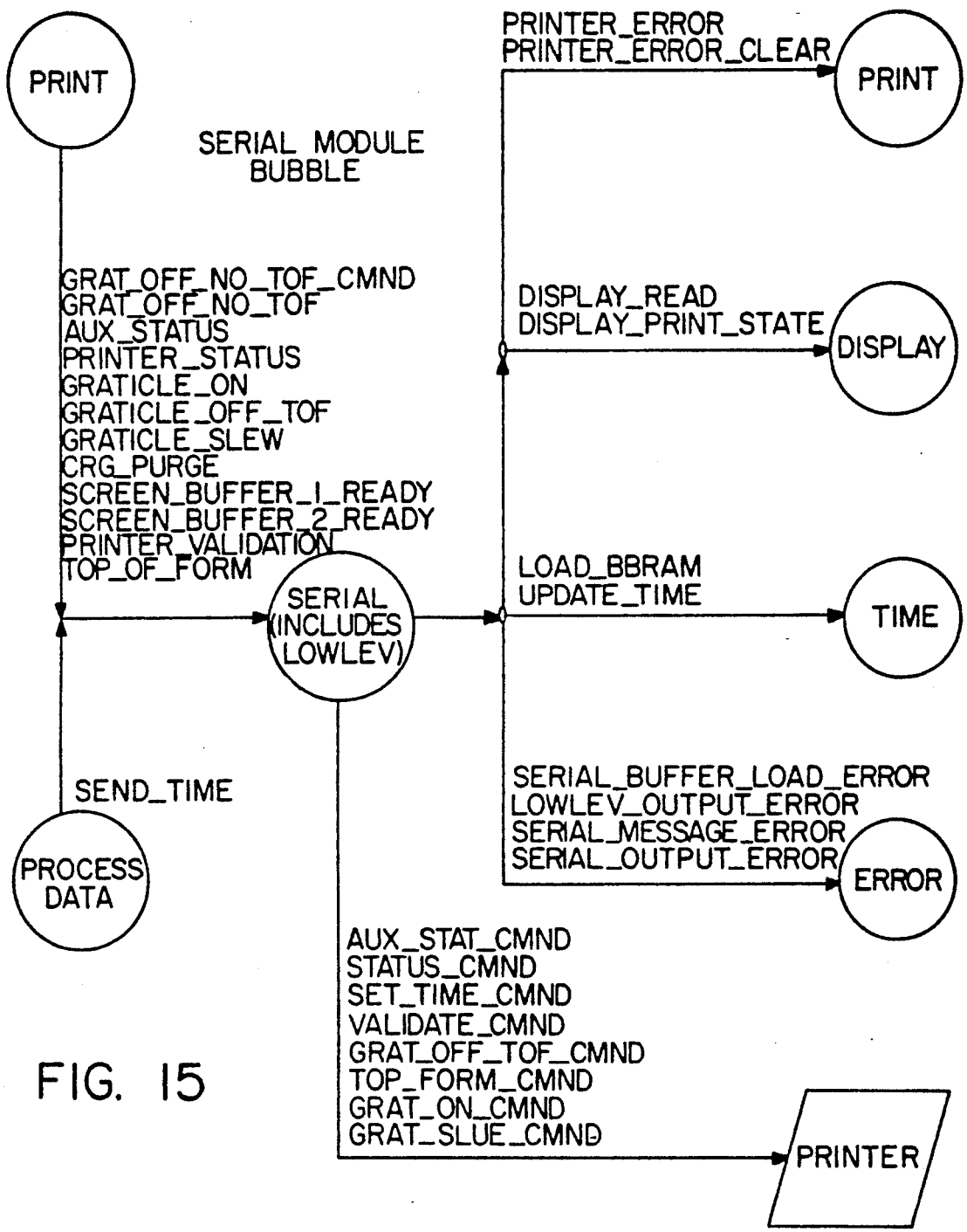
Figure 16:
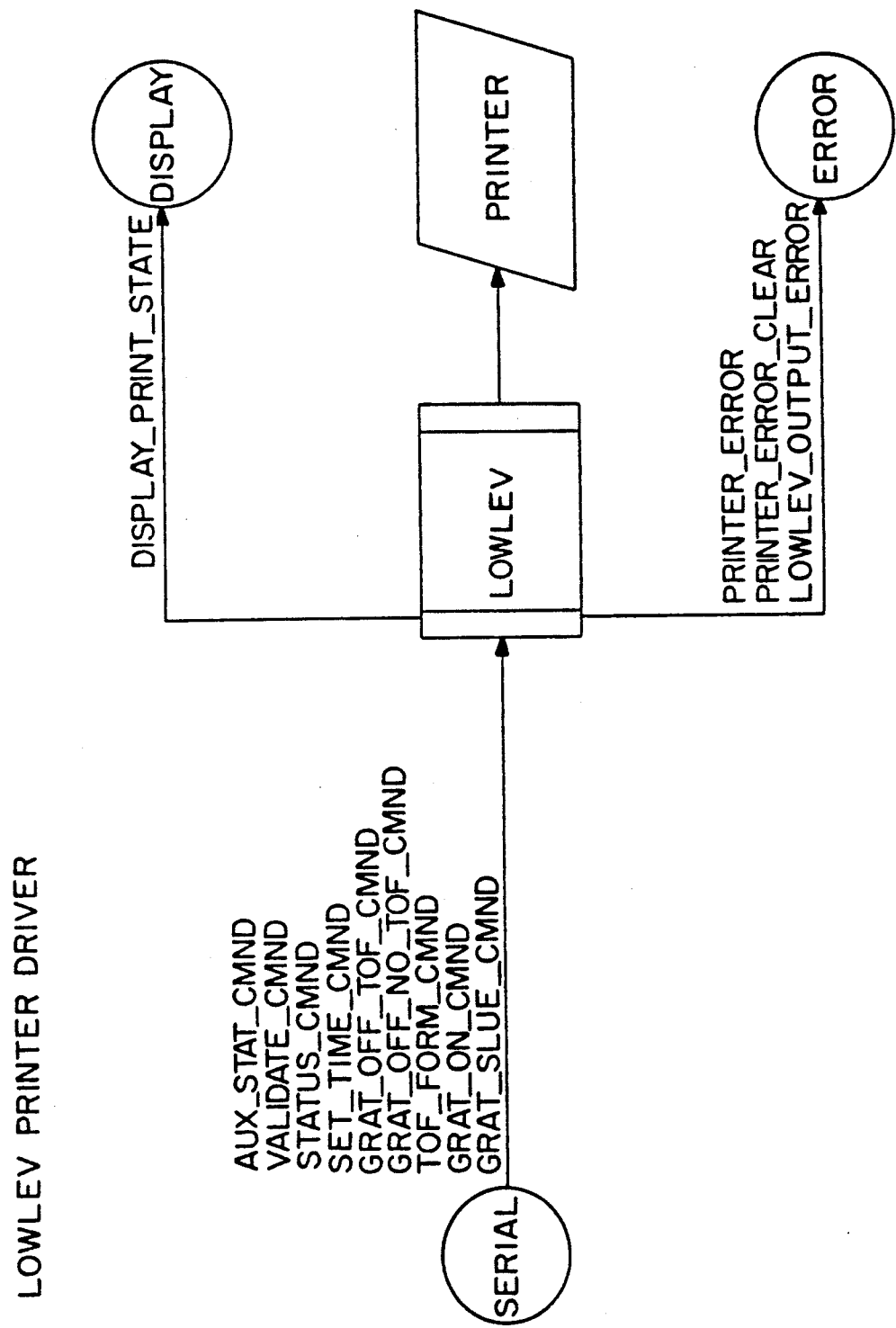

Referring now to FIGS. 15 and 16, there are shown bubble diagrams for the serial process module and for the low-level printer driver which is a sub-routine used by serial. As described above, the serial module is responsible for communication between a screen buffer controlled by display and the external printer. It is primarily controlled by messages received from the print process although process data may also transmit the current time for inclusion in a printout. Serial communicates with print by sending printer status messages, with display in order to control the buffer status, with time in order to update Battery Backed-up Random Access Memory locations, and with error for notification of inoperative conditions. The low-level routines depicted in FIG. 15 are device specific and may be altered as appropriate to control various output devices.

Figure 17:
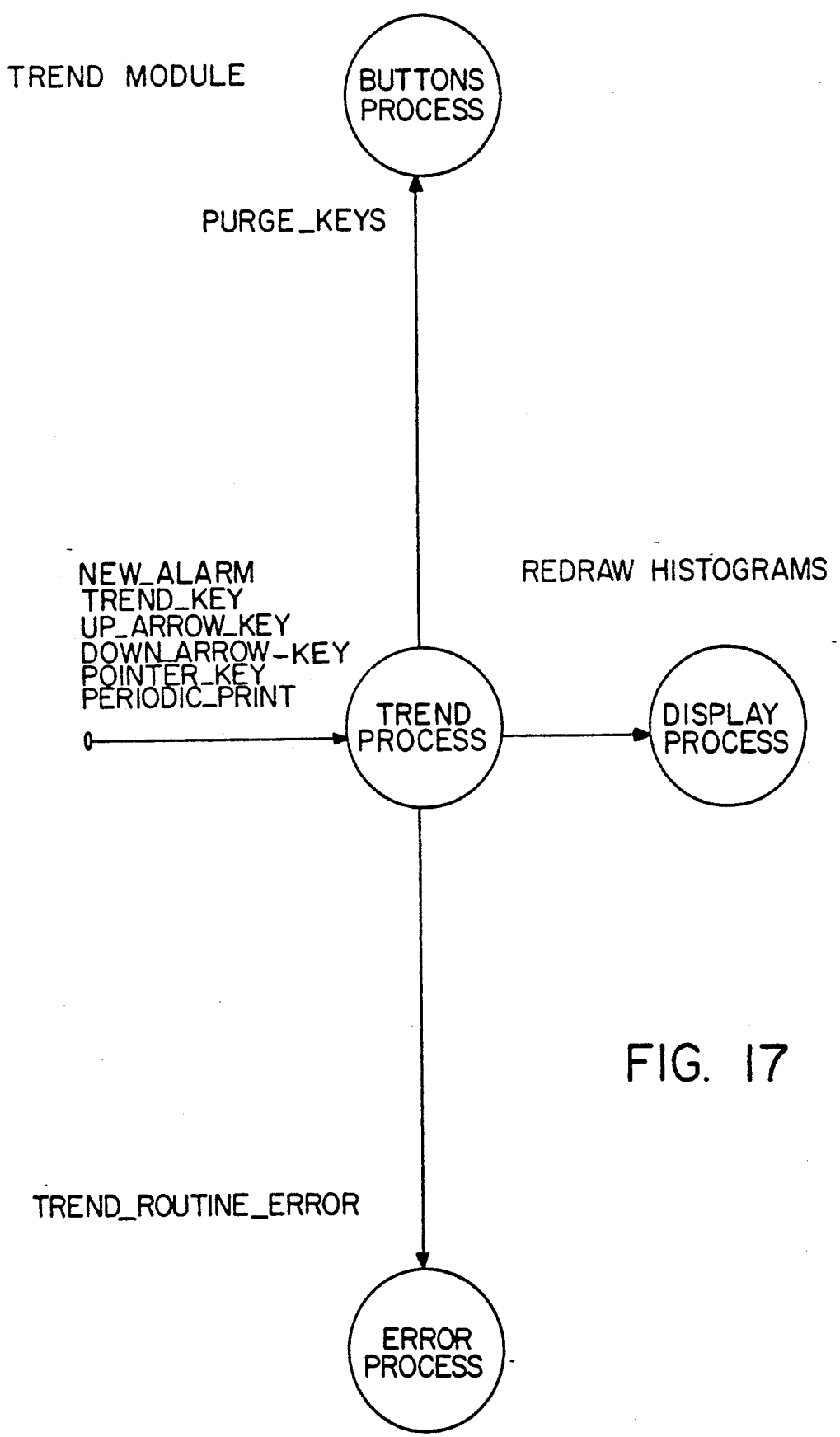

Referring now to FIG. 17, there is shown a bubble diagram of the trend process. This process has responsibility for mode changes between the main or CRG display and the trend mode displays. The trend process receives messages from the user actuation of the trend, arrow, or pointer keys as well as messages indicating the occurrence of an alarm or the demand for a normal periodic printout. It communicates messages to the buttons process in order to purge the keystroke buffer, to the display process in order to properly redraw and update screen histograms, and to the error process.

The trend module responds to key actuations of the trend key and pointer key to place the monitor system into Trend 1, Trend 2, or Trend 3 display modes. It similarly responds to indications that new alarms have occurred by switching the display back to the main or CRG display mode upon which alarms are indicated as flashing numerals. Whenever the mode is switched, trend also issues a PURGE_KEYS instruction in order to insure that additional commands are not misinterpreted after the switch.

Figure 18:
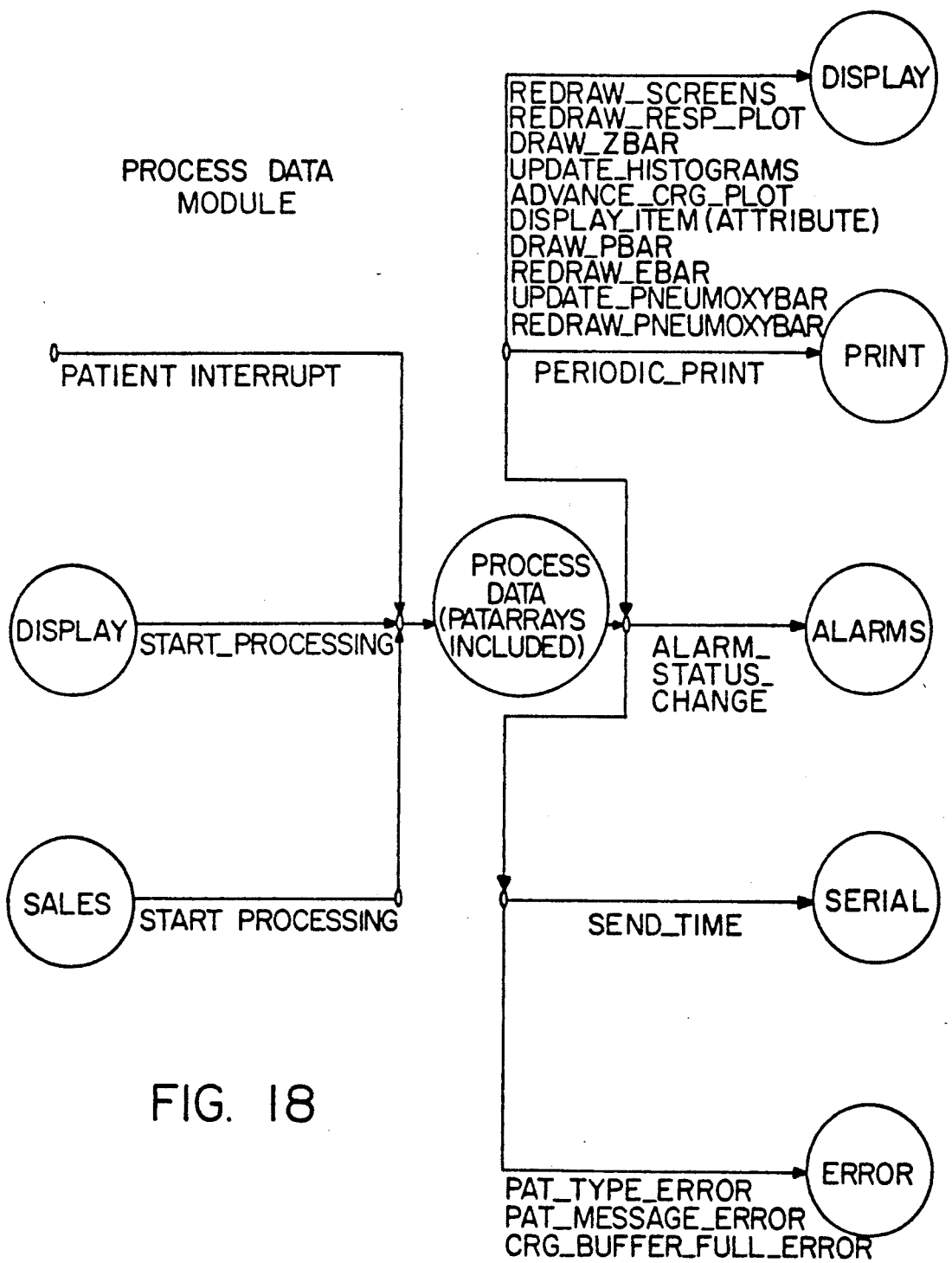

Referring now to FIG. 18, there is shown a bubble diagram of the message communication relationships of the PROCESS-DATA process. Process data receives messages from the display process and from the Sales-Demo process which indicate that it should be in processing, that is begin execution of its main routines. It also receives an interrupt from the front end board signifying that date is available. Process data carries the main responsibility for gathering patient data from the front end preprocessor, computing derived values, storing patient data in memory, and transmitting messages which cause screen and printer updates to be displayed. Process data therefore communicates with display, print, alarms, serial and error.

On system initialization, process data is placed in a message received trap and remains there until it receives a start processing message. When that message is received, process data immediately falls into an interrupt receive trap. Each interrupt is evaluated and buffered until the last interrupt in a sequence (DATA_FLAGS) is received. When DATA_FLAGS is detected, PROCESS_DATA evaluates those flags. Because each data type is generated periodically by the front end processor, and the last data type in a sequence is the DATA_FLAGS, PROCESS_DATA operates synchronously with the front end processor. Data items transmitted from the front end processor include respiration amplitude, electrocargiogram amplitude, breath detection, QRS detection, lead impedance, and any inoperative conditions sensed by the front end circuitry. In addition, saturation data may be transmitted.

Process data first calculates rates for breath and heart and includes a procedure for supplying missing data if no detection for a parameter occurs within a prescribed time period. Breath and heart rates are smoothed and these smooth numbers are used to determine alarm limit violations. Changes in alarm conditions cause a message to be sent to the alarms process. In addition, auto-scaling subroutines for both respiration and ECG adjust the displayed scale over three selectable ranges in order to conform to the received data.

Another important function of PROCESS_DATA is display updating. Various timers (for instance 2 seconds, 5 seconds, 5 minutes, etc.) determine the frequency with which particular display items are redrawn or updated. In the preferred embodiment of the present invention, the impedance or Z bar is updated every five seconds, the smoothed rate and oxyhemoglobin saturation are updated every two seconds, and the trend displays are updated every five minutes. The perfusion or P bar is also updated every five seconds. Finally, computed information is stored in memory arrays which are accessed by the display and print processes, particularly those processes associated with trend displays.

Figure 19:
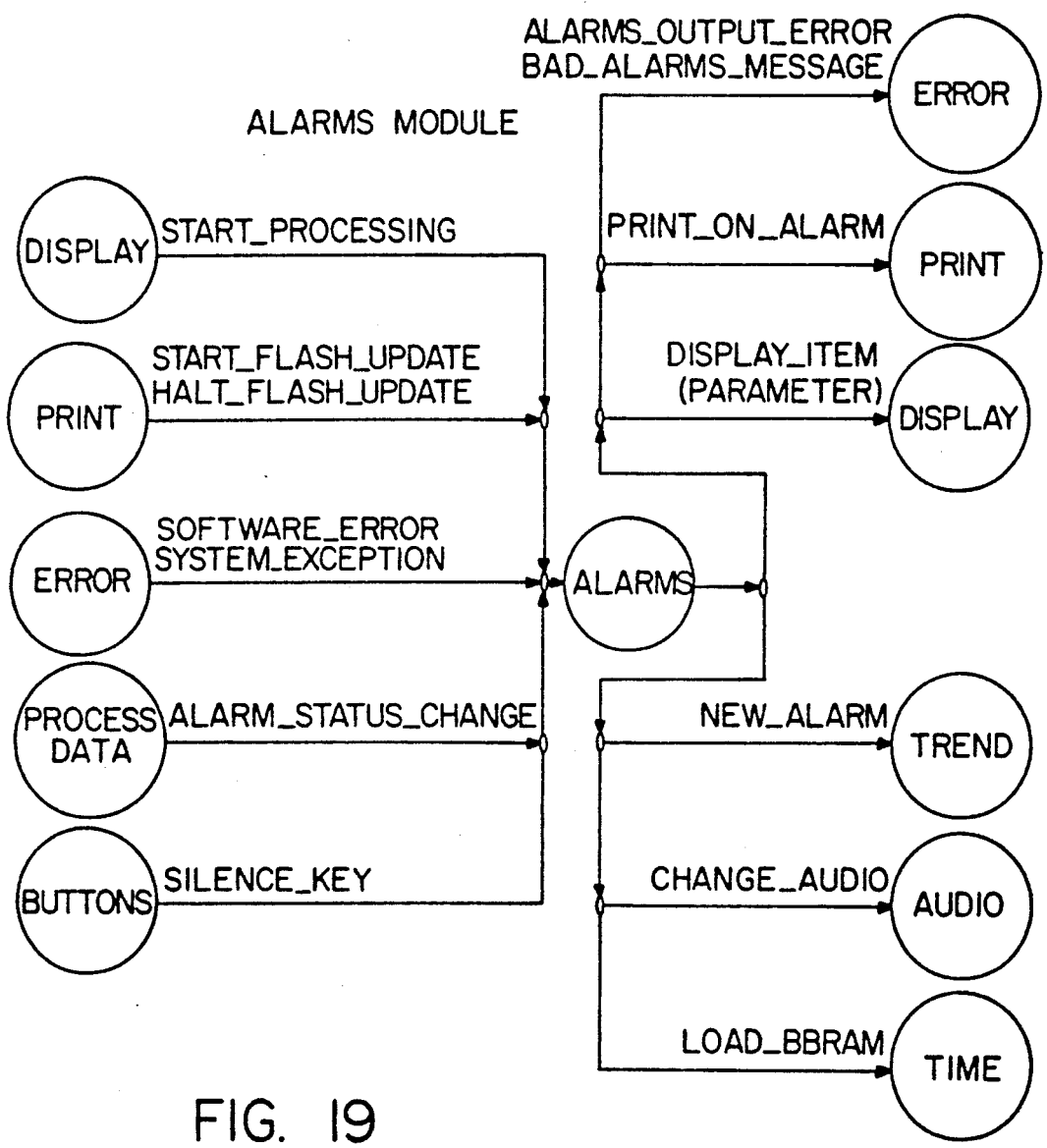

Referring now to FIG. 19, there is shown a bubble chart diagram of the message interrelationships for the alarms module. The alarms module is an intermediary module which coordinates audible and visual alarm indications which are requested by PROCESS-DATA with the specifications for alarm actuation as reflected in the operator's manual. Alarms receives requests for alarm actuation from PROCESS_DATA and from ERROR and requests for alarm inhibition from print and buttons. The display process initiates alarm processing with a start process message. Alarms communicates with six separate processes. The primary method for indication of an alarm condition is by communication to display, which causes a violated alarm limit to begin flashing on the video screen. A secondary communication of the alarm is an audible indication which is sent to a small process, audio which controls speaker output tones. Alarms also communicates changes in alarm state to the trend module to cause it to reverse the display to the main display; to the time module, to cause Battery Backed-up RAM to be loaded; to the print module in order to print the current state of the monitor system when an alarm occurs; and finally to error when a software error within the alarms module is detected.

On system initialization, alarms is placed in a message received trap and remains there until it receives the start processing message. At start processing, alarms first reads the actual time and stores it in a variable and then enters the sleep-conditionally trap for a short period. This is to permit the entire system to reach an equilibrium without the necessity for constantly answering alarm indications. After the sleep-conditionally trap is exited, alarms circular buffer is cleared. When alarms is activated by the kernel, it first ascertains the current time and then adjusts its internal timers to account for the time during which it was suspended. It then checks for a message waiting and determines whether it should return to a conditional sleep state. If its sleep duration is exceeded, alarms next tests for alarm conditions, including paper-out conditions in the printer, latched soft alarms, as defined in the operator's manual, inoperative conditions, system exceptions or latched software errors, or an inoperative oximeter detector. If any of these conditions is present, a soft alarm is determined to be active. Alarms then tests whether a hard alarm, as defined in the Operator's manual, is present, and if so, a flash timer is enabled.

Alarms next determines the status of its audio system. It first examines a register to determine whether any silences have been imposed upon it by actuation of the silence key. If there are none, all alarm audio is enabled. If the power up inhibit indicator is set, all alarms are inhibited until it is cleared. Three other types of silences are examined, including inoperative, two minute, and procedure or extended silence. In inoperative silence mode, soft alarms only are enabled. In two minute silence mode, neither hard alarms nor soft alarms are enabled, and in procedure silence, only soft alarms are enabled. After determination of silences, and of alarming condition, a test is made for a change in audio status. If audio status requires adjustment, a message to that effect is sent to the audio process. A similar procedure is followed for determination of visual alarms, output changes and finally a determination of the next sleep interval is made in order to optimize the frequency with which alarms must be reactivated by the kernel. Because alarms is a time sensitive function, it also maintains various counters.

Figure 20:
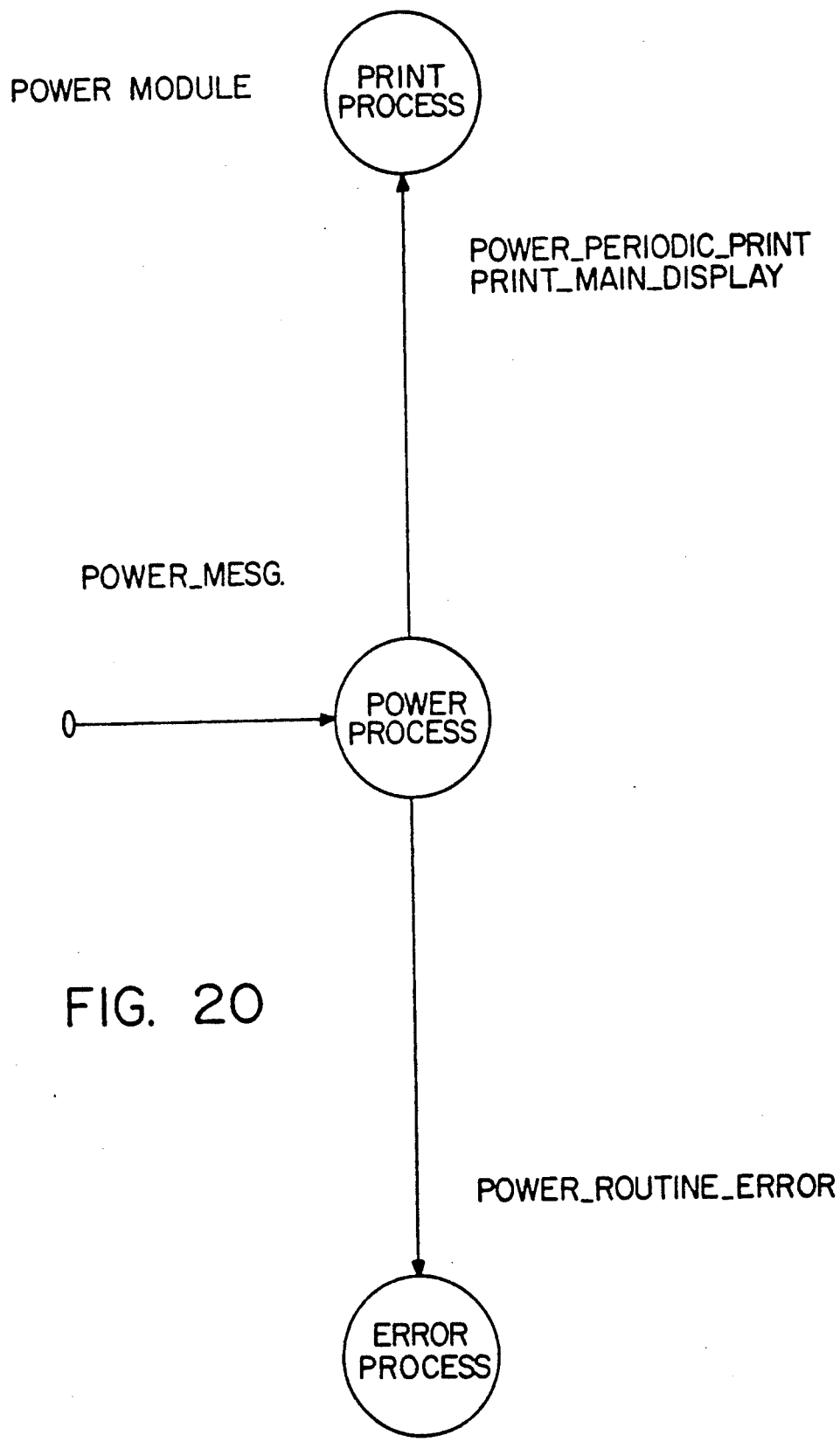

Referring now to FIG. 20, there is shown a bubble chart diagram of the POWER process. The power process simply receives power supply interrupts. POWER assesses a power supply fault or low battery condition, and upon verification, POWER instigates a full printout sequence in order to preserve historical data in memory. In addition, upon detection of the power fail indication, POWER conducts an orderly shutdown by notifying the watch-dog routine, disabling interrupt, and entering a loop until a non-maskable interrupt occurs so that the entire system may crash without the write line being in a low logic state.

Figure 21:
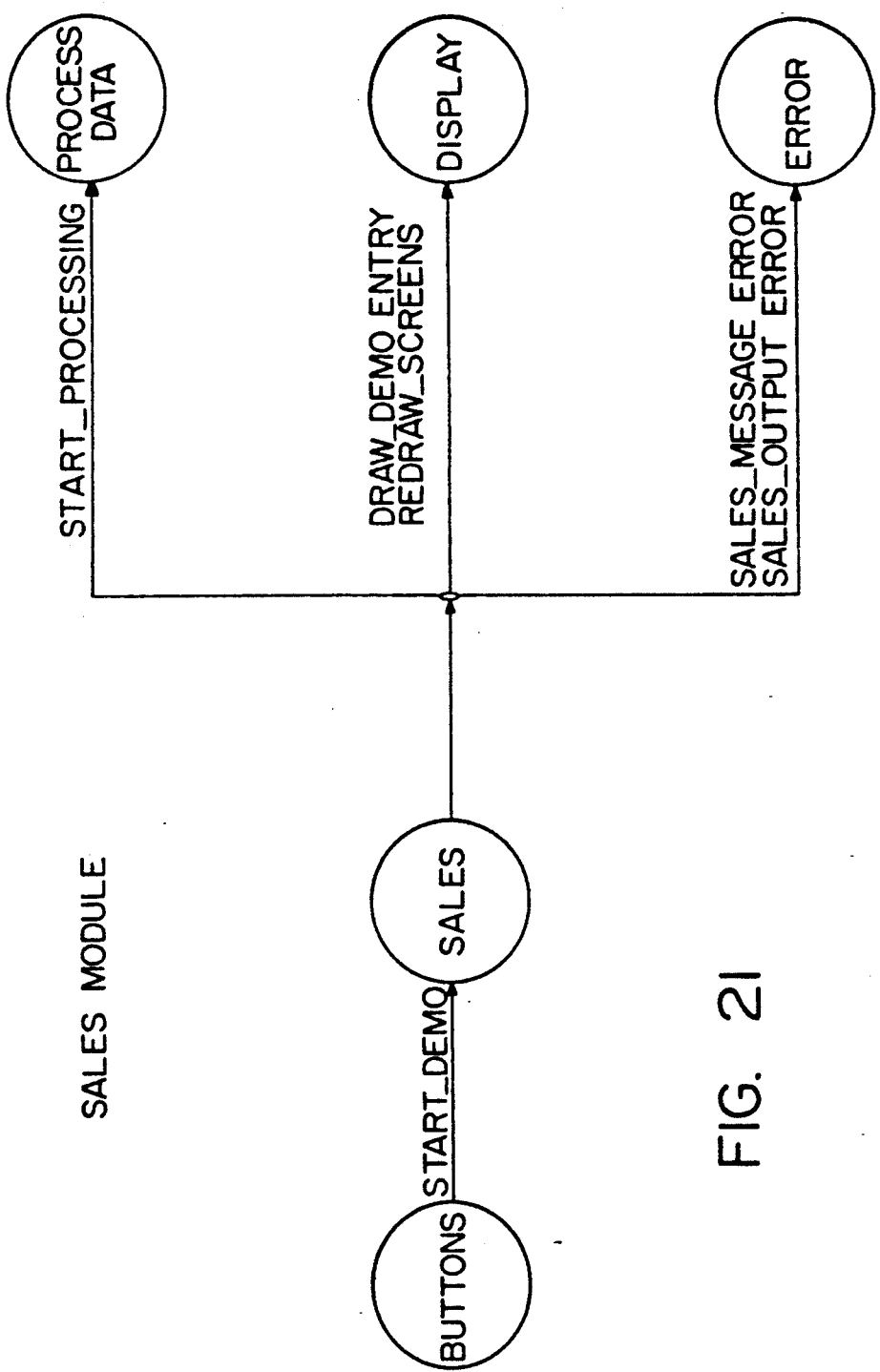

Referring now to FIG. 21, there is shown a bubble diagram for the sales process. A unique feature of the system of the present invention is the ability to simulate actual operating conditions for purposes of demonstration or training. Upon the actuation of a special key sequence at start-up time, the sales process places the entire system in a special sales mode. Sales then issues a start processing message to PROCESS_DATA, messages to DISPLAY_SCREENS to the display process, and may issue messages to ERROR, if appropriate.

Sales uses a predesigned array of trend data which is stored in read-only memory, and is relocated to active patient arrays at entry to the sales mode. In addition, the sales process simulates ECG waveform and respiratory effort waveforms which include apnea and bradycardia events. Simulation is done according to an algorithm which allows a finite pattern to recur in a predefined time period.

The sales process also includes safety features which monitor the actual connection of the system to a patient cable assembly. In the event that a patient cable is connected to the monitor system, sales will abort and reinitialize the monitor system. Exit from both the sales process and the service process is only possible by shutting down the monitor system, or by internal detection of a major system fault. (It should be noted that several of the Figures reflecting actual screen prints incorporated in both the Operator's manual and as Figures in the present application, are derived from the sales modules mode, and are marked as such).

It will be appreciated by those skilled in the art that the foregoing description should be taken in concert with microfiche Appendix 1 as constituting a full and complete description of an embodiment of the system of the present invention.

STATEMENT OF INDUSTRIAL UTILITY

The system and method of the present invention is useful in monitoring and assessing the medical condition of newborn infants for the occurrence of apnea and apnea coupled with bradycardia.

What is claimed is:

1. A method for displaying historical information related to apnea events in a human infant comprising the steps of:
   a) producing signals indicative of cardiac activity, and respiratory effort;
   b) transmitting said produced signals to a computer;
   c) receiving said signals into said computer;
   d) calculating smoothed instantaneous heart rate, respiratory effort, transthoracic impedance, and smoothed instantaneous respiration rate;
   e) detecting apnea and bradycardia events, storing data indicative of said events, and simultaneously displaying to a user on a single visual display:
      1) a first histogram showing the absolute number of apnea events for each of a predetermined number of time intervals over a predetermined period;
      2) a numeric indication of the absolute number of apnea events during said predetermined period; and
      3) a second histogram showing the absolute number of apnea events for each of a predetermined number of durations during said predetermined period.

2. The method of claim 1 wherein said histograms further indicate visually the number of said apnea events which coincide in time with bradycardia events.

3. A method for displaying historical information related to apnea events in a human infant comprising the steps of:
   a) producing signals indicative of cardiac activity, and respiratory effort;
   b) transmitting said produced signals to a computer;
   c) receiving said signals into said computer;
   d) calculating smoothed instantaneous heart rate, respiratory effort, transthoracic impedance, and smoothed instantaneous respiration rate;
   e) selecting a time interval of interest to a user;
   f) detecting apnea and bradycardia events, storing data indicative of said events, and simultaneously displaying to a user on a single visual display:
      1) a first histogram showing the absolute number of apnea events for each of a predetermined number of time intervals over a predetermined period;
      2) a numeric indication of the absolute number of apnea events during said selected time interval; and
      3) a second histogram showing the absolute number of apnea events for each of a predetermined number of durations during said selected time interval.

4. The method of claim 3 wherein said histograms further indicate visually the number of said apnea events which coincide in time with bradycardia events.

5. The method of claim 3 wherein apnea-coupled bradycardia is indicated when said smoothed instantaneous heart rate falls below a value less than 80% of a rate calculated by averaging a predetermined number of immediately preceding rate values, and apnea has been detected.

6. The method of claim 3 wherein apnea-coupled bradycardia is indicated when said smoothed instantaneous heart rate falls below a value less than a user-defined value, and apnea has been detected.

7. A method for displaying historical information related to apnea events in a human infant comprising the steps of:
   a) producing signals indicative of cardiac activity, and respiratory effort;
   b) transmitting said produced signals to a computer;
   c) receiving said signals into said computer;
   d) calculating smoothed instantaneous heart rate, respiratory effort, transthoracic impedance, and smoothed instantaneous respiration rate;
   e) selecting an apnea duration of interest to a user;
   f) detecting apnea and bradycardia events, storing data indicative of said events, and simultaneously displaying to a user on a single visual display:
      1) a first histogram showing the absolute number of apnea events for said selected duration for each of a predetermined number of time intervals over a predetermined period;
      2) a numeric indication of the absolute number of apnea events for said selected duration during said predetermined period; and
      3) a second histogram showing the absolute number of apnea events for each of a predetermined number of durations during said predetermined period.

8. A method for displaying historical information related to apnea events in a human infant comprising the steps of:
   a) producing signals indicative of cardiac activity, and transthoracic impedance;
   b) transmitting said produced signals to a computer;
   c) receiving said signals into said computer;
   d) calculating smoothed instantaneous heart rate, smoothed instantaneous oxyhemoglobin saturation, average oxyhemoglobin saturation over a predetermined time interval, minimum and maximum oxyhemoglobin saturation over said predetermined time interval, respiratory effort, transthoracic impedance, and smoothed instantaneous respiration rate;

e) detecting apnea and bradycardia events, storing data indicative of said events, and simultaneously displaying to a user on a single visual display:

1) a first histogram showing the absolute number of apnea events for each of a predetermined number of said time intervals over a predetermined period;

2) a numeric indication of the absolute number of apnea events during said predetermined period; and 3) a second histogram showing the maximum, minimum and average oxyhemoglobin saturation for each of a predetermined number of durations during said predetermined period.

9. The method of claim 8 wherein said first histogram further indicates visually the number of said apnea events which coincide in time with bradycardia events.

* * * * *